(12) United States Patent
Dewey et al.

(10) Patent No.: US 8,523,847 B2
(45) Date of Patent: Sep. 3, 2013

(54) RECONNECTABLE HANDPIECES FOR OPTICAL ENERGY BASED DEVICES AND METHODS FOR ADJUSTING DEVICE COMPONENTS

(75) Inventors: David A. Dewey, Sunnyvale, CA (US); Gary Porter, Redwood City, CA (US)

(73) Assignee: Reliant Technologies, Inc., Hayward, CA (US)

( * ) Notice: Subject to any disclaimer, the term of this patent is extended or adjusted under 35 U.S.C. 154(b) by 1307 days.

(21) Appl. No.: 12/264,793

(22) Filed: Nov. 4, 2008

(65) Prior Publication Data

US 2009/0131922 A1    May 21, 2009

Related U.S. Application Data

(60) Provisional application No. 60/986,181, filed on Nov. 7, 2007.

(51) Int. Cl.
    *A61B 18/18*    (2006.01)

(52) U.S. Cl.
    USPC .......................................................... 606/9

(58) Field of Classification Search
    USPC ................... 606/1–19; 607/88–94
    See application file for complete search history.

(56) References Cited

U.S. PATENT DOCUMENTS

| 7,184,184 B2 | 2/2007 | DeBenedictis et al. |
| 7,196,831 B2 | 3/2007 | Broome et al. |
| 7,282,060 B2 | 10/2007 | DeBenedictis et al. |
| 2001/0025173 A1* | 9/2001 | Ritchie et al. ............... 606/10 |
| 2002/0087179 A1* | 7/2002 | Culp et al. .................. 606/167 |
| 2002/0109671 A1* | 8/2002 | Kawasome .................. 345/156 |
| 2002/0156466 A1* | 10/2002 | Sakurai et al. ............... 606/1 |
| 2003/0216719 A1 | 11/2003 | Debenedictis et al. |
| 2005/0049582 A1 | 3/2005 | DeBenedictis et al. |
| 2005/0285928 A1 | 12/2005 | Broome et al. |
| 2006/0095096 A1 | 5/2006 | DeBenedictis et al. |
| 2007/0093797 A1* | 4/2007 | Chan et al. .................. 606/12 |
| 2008/0024447 A1* | 1/2008 | Hsieh et al. ................. 345/163 |
| 2008/0077200 A1* | 3/2008 | Bendett et al. .............. 607/89 |

* cited by examiner

*Primary Examiner* — Ryan Severson
*Assistant Examiner* — David Eastwood
(74) *Attorney, Agent, or Firm* — Wood, Herron & Evans LLP

(57) ABSTRACT

Handpieces which comprise characteristic data storage systems electronically storing characteristic data, devices comprising these handpieces, methods of characterizing the device components, and methods of adjusting the device components based on stored characteristic data are described. The handpieces can be repeatedly connected to, disconnected from, and reconnected to an optical energy system comprising at least one optical energy source and at least one controller by a treatment provider. When the handpieces are connected to an optical energy source and a controller, the component characteristic data is accessed and used to adjust one or more of the components in order for the components to function together within a pre-determined tolerance. Once the components are connected and adjusted, the device can be used to provide an optical energy based medical and/or cosmetic treatment to a tissue such as, for example, human skin.

25 Claims, 5 Drawing Sheets

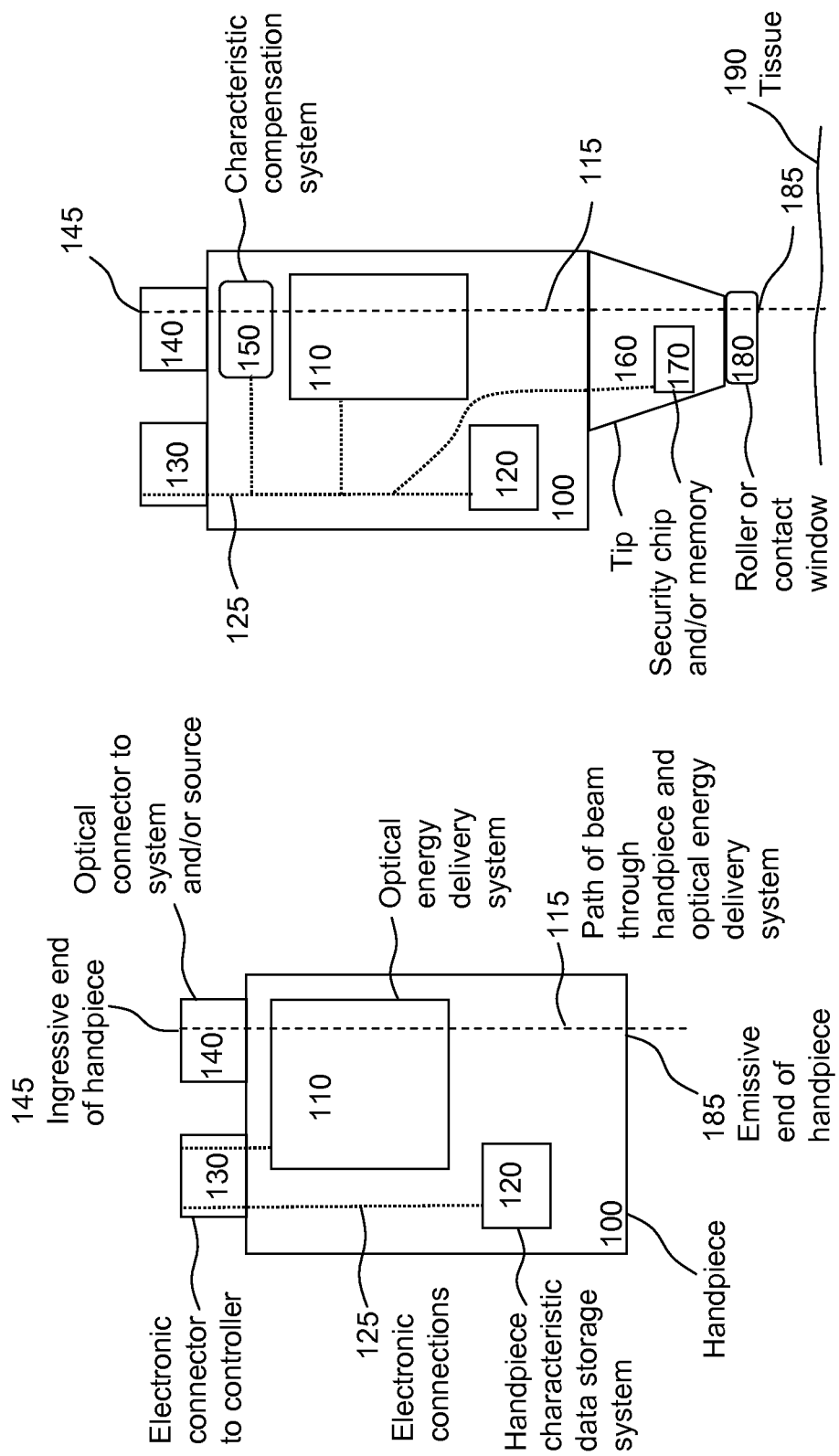

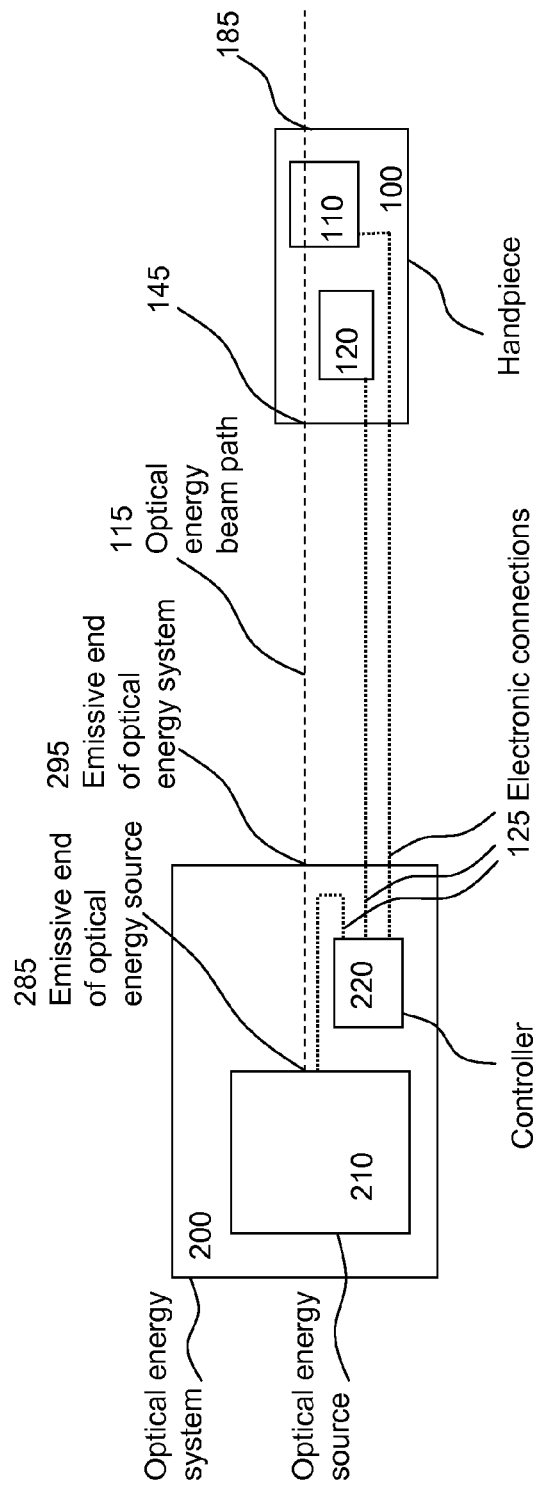
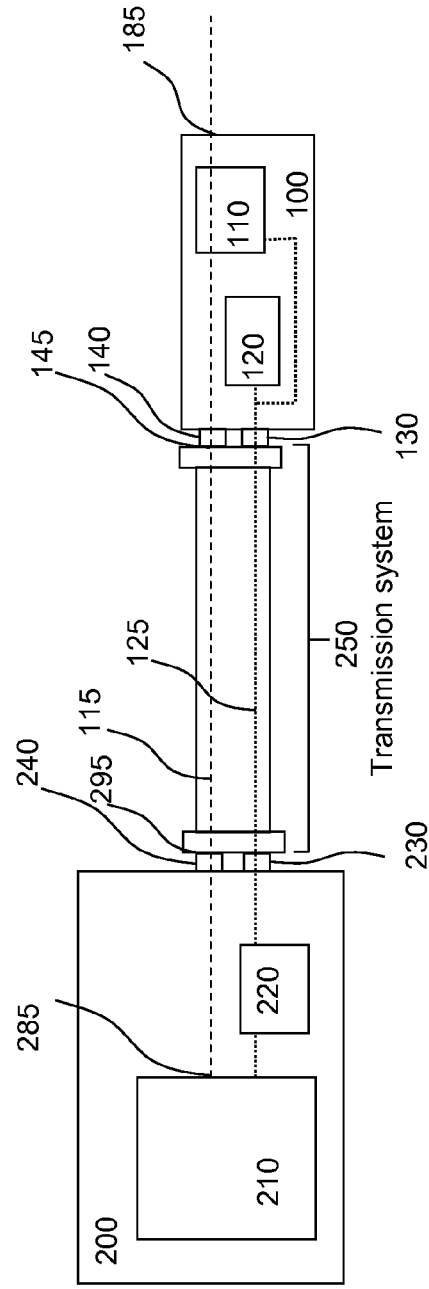
FIG. 2A
FIG. 2B

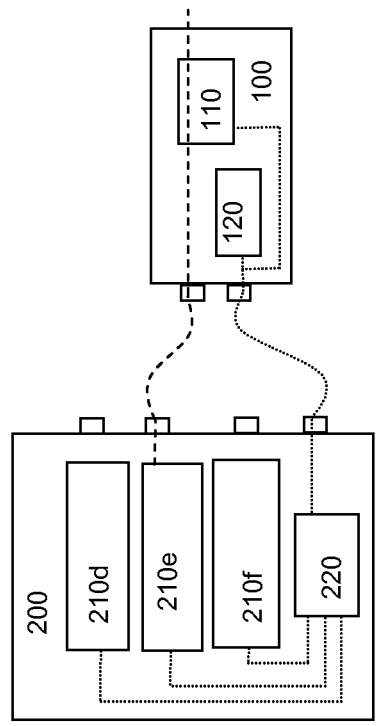
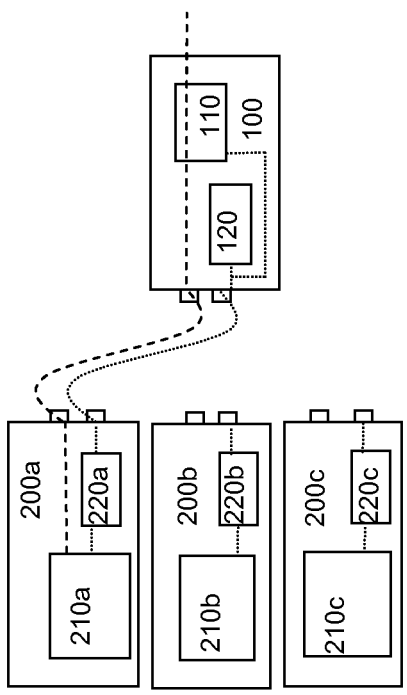
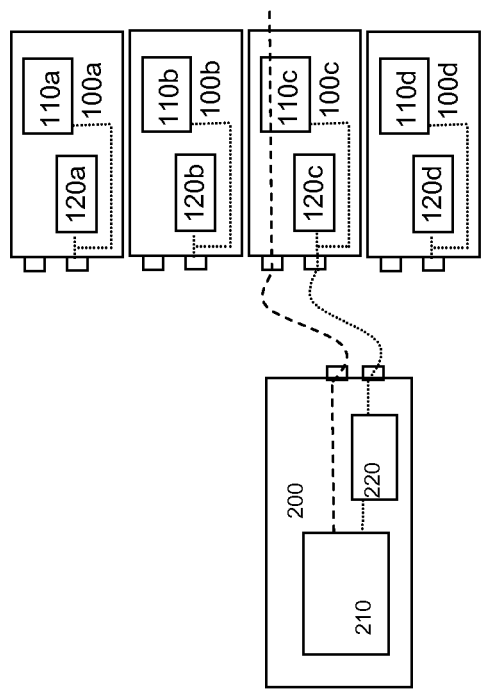

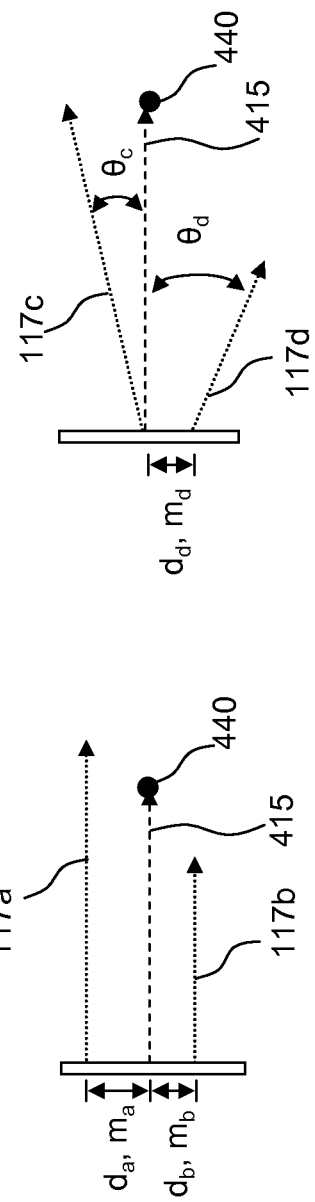

RECONNECTABLE HANDPIECES FOR OPTICAL ENERGY BASED DEVICES AND METHODS FOR ADJUSTING DEVICE COMPONENTS

CROSS-REFERENCE TO RELATED APPLICATION(S)

This application claims priority under 35 U.S.C. §119(e) to U.S. Provisional Patent Application Ser. No. 60/986,181, "Reconnectable Handpieces for Optical Energy Based Devices and Methods for Adjusting Device Components," filed Nov. 7, 2007 by David A. Dewey and Gary Porter. The subject matter of the foregoing is incorporated herein by reference in its entirety.

FIELD OF THE INVENTION

The present invention relates generally to methods and devices for delivering optical energy, and in particular to reconnectable handpieces for delivering optical energy which have characteristic data electronically stored in them, medical and/or cosmetic treatment devices comprising these reconnectable handpieces, methods of characterizing the handpieces and/or the optical energy producing components of the devices, and methods of adjusting the handpieces and/or the optical energy producing components of a device based on the stored characteristic data in order to make the handpieces and the optical energy producing components function together within pre-determined tolerances.

BACKGROUND OF THE INVENTION

Optical energy, particularly laser energy, is commonly used for industrial purposes, for example, to cut or weld materials. Optical energy is also commonly used as a versatile tool in medicine to achieve desired outcomes in a tissue that is treated. For example, lasers and other forms of intense light have been used to treat common dermatological problems such as hypervascular lesions, pigmented lesions, acne scars, rosacea, and/or for hair removal. Forms of optical energy are also used for cosmetic purposes, to achieve a better cosmetic appearance by resurfacing the skin, by remodeling the different layers of skin to improve the appearance of wrinkled or aged skin, and/or by tightening the skin. Generally, skin resurfacing is understood to be the process by which the top layers of the skin are completely removed using chemicals, mechanical abrasion or optical energy in order to promote the development of new, more youthful looking skin and stimulate the generation and growth of new skin. In laser skin remodeling, laser energy penetrates into at least a portion of the deeper layers of the skin and is aimed at stimulating the generation of and/or altering the structure of extra-cellular matrix materials, such as collagen, that contribute to the youthful appearance of skin.

During dermatological tissue treatments utilizing optical energy, a beam of optical energy irradiates the surface of a patient's skin. Generally, optical energy based devices that are used for such treatments operate at wavelengths that are absorbed by one or more absorbing species naturally present in the skin, such as, for example, melanin, hemoglobin, or water, although exogenous absorbing species can also be added to the tissue. In the case when water is used as the primary absorbing species, cellular and interstitial water absorbs optical energy and transforms the optical energy into thermal energy. The transport of thermal energy in tissues during treatment is a complex process involving conduction, convection, radiation, metabolism, evaporation and phase change that vary with the functional parameters of the beam of optical energy. It is important in such procedures not to damage tissue underlying or surrounding the target area of tissue. If the functional parameters of the optical energy, such as, for example, wavelength, beam energy density, and/or beam pulse duration, are properly selected, cellular and interstitial water in the patient's skin is heated, causing temperature increases that produce a desired effect. Conversely, improper selection of the functional parameters can result in under-treatment or over-treatment of the tissue. Therefore, it is desirable to accurately control the functional parameter settings used by the treatment device so that the optical energy is delivered to the tissue in a uniform, controlled manner.

Many of the currently marketed medical and/or cosmetic optical energy based devices are used in direct contact with tissue being treated, or can have tissue deposited on them by the treatment process over the course of a treatment. Such devices require cleaning and special care to maintain cleanliness. Such devices can additionally require cleaning to maintain the efficacy of the treatment, as their delivery systems often include a window or some aperture through which the optical energy passes. If these windows or apertures become blocked for example, by foreign substances, scratches, chips, or cracks, then the device typically will not function properly. Conventional devices typically have a monolithic handpiece with unchangeable mechanical, electrical and optical components and connections, which can be difficult to adequately clean and/or sterilize.

A typical method of using conventional monolithic handpieces to deliver an optical energy based treatment is to produce a macroscopic, pulsed treatment beam that is manually moved from one area of the skin to another in a patchwork-like manner or a stamping manner (i.e., the handpiece is not in motion when the treatment beam is applied) in order to treat a larger portion of tissue. Such an approach can have the disadvantage of producing artifacts and sharp boundaries associated with the inaccurate positioning of the individual treatments with respect to the treated skin surface.

More recently, devices are being marketed which employ handpieces which are capable of delivering a treatment as the handpiece is moved across the portion of tissue to be treated. Employing handpieces which can deliver treatment while in motion requires more complex engineering and presents a new set of difficulties for the treatment provider, such as the requirement to maintain one constant treatment speed. More complex handpieces have overcome this limitation by using handpiece speed feedback to automatically adjust functional parameters of the device in order to compensate for handpiece speed and deliver a uniform, controlled treatment.

Increasingly, conventional bulk skin treatment methods are being replaced by fractional treatment methods, as the use of fractional treatment methods has been found to produce fewer and less severe side effects than conventional bulk treatment methods, such as, for example, reduced damage to the epidermal layers of the skin. Fractional treatment methods involve the generation of a large number of treatment zones within a portion of tissue. The optical energy impacts directly on only the relatively small treatment zones, instead of impacting directly on the entire portion of tissue undergoing treatment, as it does in conventional bulk treatments. Thus, a portion of skin treated using a fractional optical energy treatment method is composed of a number of treatment zones where the tissue has been treated directly by the energy, contained within a volume of tissue that has not been treated directly by the energy. The treatment can, for example, produce coagulation and/or necrosis of tissue. Fractional treatment methods make it possible to leave substantial volumes of tissue untreated (e.g., uncoagulated and/or viable) within a portion of tissue that has been treated.

Devices which are capable of providing fractional treatments typically employ a means to scan one or more beams of optical energy across a portion of tissue, or a means to divide one or more beams of optical energy into a plurality of beams, and deliver the plurality of beams to a portion of tissue to be treated. These additional scanning or dividing components are often located in the handpiece, making the handpieces for fractional treatment devices more complex than the handpieces for bulk treatment devices.

Complex handpieces, such as those that deliver uniform, controlled treatments while in motion and/or those which include optical delivery systems that deliver energy in a fractional manner, can require the use of high manufacturing tolerances and/or the use of great precision when connecting the optical components of the handpiece as well as the rest of the device in order for the components of the device to function properly and for the device to deliver the optical energy in an efficient, effective, uniform and controlled manner. For example, a large number of functional parameters need to be properly set in order for an optical energy system and/or source to function properly on its own. Similarly, a large number of functional parameters need to be properly set in order for a handpiece and its optical energy delivery system (e.g., scanner, lens array, or other means for delivering the treatment beam(s) to the portion of tissue) to function properly on their own, as well as to function properly in conjunction with an optical energy system and/or source.

For example, conventional bulk optical energy-based treatments have typically been delivered using a monolithic handpieces containing a few non-moving optical components requiring that only a low level of precision and/or low tolerances be used in making its optical connections in order for a beam of optical energy to pass through it properly, and which do not have any functional parameters which can be adjusted. By comparison, handpieces for fractional delivery devices can contain, for example, precision scanners, lens arrays, and/or rotating wheels, and thus require a high level of coordination in terms of adjustments of functional parameters related to the beam characteristics, the optical path, timing of the beam, timing of moving components, position of moving parts, and/or energy settings between the components of the handpiece and the optical energy system and/or source. Due to the high level of precision required to manufacture and align the optical components, the large number of characteristics which must be determined for the components of the device, and the large number of functional parameters which must be properly set for such devices to function properly, properly adjusting and aligning the components of these devices is not easily done outside the manufacturing setting, and cannot easily be done by a treatment provider. For this reason, the marketed treatment devices employing sophisticated optical energy sources and handpieces have been composed of handpieces and optical energy sources which can only be disconnected and reconnected in a manufacturing setting, and/or by a trained technician outside a manufacturing setting.

Not being able to have the treatment provider easily connect, disconnect, and reconnect the handpieces and/or the optical energy systems and/or sources of these devices limits the utility of the devices, as it can require that a treatment provider purchase a dedicated device for each possible type of treatment, rather than purchasing a device composed of one or more reconnectable handpieces and/or one or more reconnectable optical energy sources which can be combined in different configurations in order to deliver different types of treatments.

The present invention provides devices and methods which address this need by providing reconnectable handpieces, devices comprising reconnectable handpieces and optical energy systems and/or sources, methods of establishing characteristic data of device components, and methods of using the established characteristic data to adjust the components of a device in order for the components to function together properly after being connected. The method of using the established characteristic data to adjust the components of the device uses a controller to access stored characteristic data and make any necessary adjustments to parameter settings, and so can be easily executed by a treatment provider in the location where the device is to be used.

SUMMARY OF THE INVENTION

In general, the present invention is directed to handpieces used to deliver optical energy that have characteristic data electronically stored in them, to devices comprising these handpieces, to methods of establishing stored characteristic data in a device component such as a handpiece, and to methods of adjusting connected device components using stored characteristic data. The handpieces, devices and methods of the present invention can be used to deliver optical energy to a material, to provide medical and/or cosmetic treatments to tissue, and/or to provide dermatological treatments to human skin.

A device of the present invention can comprise one or more reconnectable handpieces, one or more optical energy sources, such as, for example, a laser or intense pulsed light source, and one or more controllers. A reconnectable optical energy system can comprise one or more optical energy sources and one or more controllers, wherein the system is configured to be connected to one or more handpieces. When an optical energy system (i.e., an optical energy source and a controller) is connected to a handpiece, the combination is considered to be a device. One or more handpieces, or a set of handpieces, can be interchangeably attached to an optical energy system and/or source, for example, to alter the beam spot size, the beam pattern, and/or the treatment coverage area. Alternatively, a handpiece can be interchangeably attached to one or more optical energy systems and/or sources, or with a set of optical energy systems and/or sources, for example, to provide a treatment using a specific wavelength or combination of wavelengths of optical energy, a treatment intended to treat a specific disease or condition, and/or a treatment intended to target a specific absorbing species or a specific component of tissue.

In one aspect, the invention is directed to a handpiece for a medical and/or cosmetic treatment device, comprising: at least one optical energy delivery system configured to direct optical energy at a portion of tissue to be treated, and at least one handpiece characteristic data storage system which electronically stores characteristic data, wherein the handpiece is configured to be repeatedly reconnected to one or more optical energy systems and/or sources, and the handpiece is configured to be adjusted based on the characteristic data so as to allow the handpiece to operate with the one or more optical energy systems and/or sources within a pre-determined tolerance. The characteristic data can comprise handpiece characteristic data, optical energy system and/or source characteristic data, and/or combined handpiece/optical energy system and/or source characteristic data. The characteristic data can comprise a distance-based value which is converted to a time-based value prior to or following storage, or a time-based value that is converted to a distance-based value prior to or following storage.

In another aspect, the invention is directed to a medical and/or cosmetic treatment device comprising: at least one optical energy source; at least one controller; and at least one handpiece, each handpiece comprising at least one optical energy delivery system, and at least one handpiece characteristic data storage system which electronically stores characteristic data; wherein the at least one handpiece is configured to be repeatedly reconnected to the device; the at least one energy source and the at least one handpiece are configured such that, when one handpiece of the at least one handpiece and the at least one energy source are operably coupled, the at least one optical energy source produces a beam of optical energy that exits an emissive end of the at least one optical energy source, enters an ingressive end of the one handpiece, passes through the at least one optical energy delivery system of the one handpiece, and passes out of an emissive end of the one handpiece in order to treat a portion of tissue; and the controller is configured to control the at least one optical energy source and the at least one handpiece, to access the characteristic data stored in the at least one handpiece characteristic data storage system, and to adjust one or more parameter settings of the at least one optical energy source and/or the at least one handpiece based on the characteristic data in order for the at least one handpiece to operate with the at least one optical energy source within a pre-determined tolerance.

In another aspect, the invention is directed to a method of characterizing a component for use in an optical energy treatment device, comprising: determining characteristic data of a beam and/or beam path as the beam of optical energy passes through and/or exits the component, and electronically storing the characteristic data in a characteristic data storage system. In one example, the component comprises an optical energy system and/or source, the characteristic data is determined as the beam and/or beam path exits the optical energy system and/or source, and the characteristic data storage system comprises an optical energy system and/or source characteristic data storage system. In another example, the component comprises a handpiece; the characteristic data is determined as the beam enters the ingressive end of the handpiece, enters a component of the handpiece, exits the component of the handpiece, and/or exits the emissive end of the handpiece; and the characteristic data storage system comprises a handpiece characteristic data storage system. In yet another example, the component comprises an optical energy transmission system, the characteristic data is determined as the beam and/or beam path enters the ingressive end of the transmission system and/or exits the emissive end of the transmission system, and the characteristic data storage system comprises a transmission system characteristic data storage system. The method can further comprise the step of converting at least one piece of the characteristic data from a distance-based value to a time-based value, or from at time-based value to a distance-based value. The stored characteristic data can further comprise information about the component that is not determined during the determining step.

In another aspect, the invention is directed to a method of adjusting a handpiece and an optical energy system and/or source for use in an optical energy treatment device, comprising: attaching a handpiece to an optical energy system and/or source, accessing characteristic data stored in a handpiece characteristic data storage system, determining at least one parameter setting based on the characteristic data stored in the handpiece characteristic data storage system, and adjusting at least one operational parameter of the handpiece and/or of the optical energy system and/or source based on at least one determined parameter setting. In one example, the step of determining can comprise converting the characteristic data from a distance-based value to a time-based value, or from a time-based value to a distance-based value. The method can further comprise the step of accessing characteristic data stored in an optical energy system and/or source characteristic data storage system, and determining at least one parameter setting based on the characteristic data stored in the optical energy system and/or source characteristic data storage system.

Other aspects of the invention include methods, systems and applications relating to the embodiments described above.

BRIEF DESCRIPTION OF THE DRAWINGS

FIG. 1 is composed of two diagrammatic views, FIG. 1A and FIG. 1B, illustrating two examples of handpieces which can be used to deliver optical energy.

FIG. 2 is composed of two diagrammatic views, FIG. 2A and FIG. 2B, illustrating two examples of optical energy based devices, each showing a handpiece connected to an optical energy system and an optical energy source.

FIG. 3 is composed of three diagrammatic views, FIG. 3A, FIG. 3B, and FIG. 3C, illustrating three examples of optical energy based devices composed of one or more reconnectable handpieces, and one or more reconnectable optical energy systems and/or sources and controllers.

FIG. 4 is composed of two drawings, FIG. 4A and FIG. 4B, both illustrating types of characteristic data that can be used to characterize a beam and/or a beam path.

FIG. 5 is composed of three drawings, FIG. 5A, FIG. 5B, and FIG. 5C illustrating diagrammatic views of a handpiece comprising a handpiece characteristic data storage system and an optical energy delivery system employing a starburst scanner.

DETAILED DESCRIPTION OF THE PREFERRED EMBODIMENTS

Figure 5C:
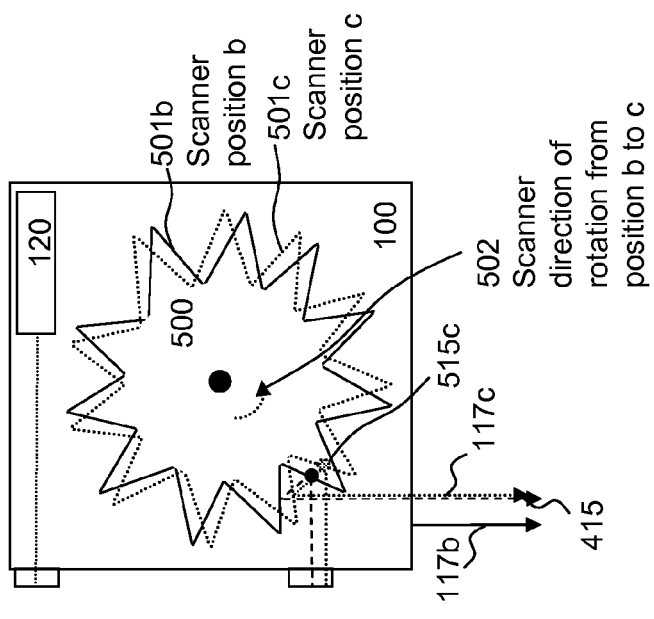
FIG. 5C illustrates the optimal beam path, the actual beam path after adjustment, and the parameter which was adjusted in order to adjust the actual beam path.

Medical devices which deliver optical energy, such as, for example, devices used to deliver medical and/or cosmetic tissue treatments, typically include a delivery apparatus of some type. One example of a delivery apparatus is a handpiece. While generally a handpiece is designed to be held in the hand of a user or a treatment provider (e.g., a physician, a medical professional, a cosmetic professional, and/or a consumer) and used to apply energy to skin, for the purposes of the present invention, a handpiece will be understood to more broadly mean any apparatus which is configured to be used to delivery optical energy to a biological tissue. Thus, a handpiece can be controlled manually. In one example, a handpiece can be configured to be used by a treatment provider to direct optical energy from an energy source to a tissue to be treated so as to deliver a safe and effective treatment to the tissue.

For the purposes of the present invention, a handpiece will be understood to comprise an optical energy delivery system which directs the optical energy, and a data storage system which electronically stores at least one piece of characteristic data, where the handpiece is configured to be repeatedly reconnected to one or more optical energy systems and/or sources, and the handpiece is configured to be adjusted based on the characteristic data so as to allow the handpiece to operate with the one or more optical energy system and/or sources within a pre-determined tolerance. A handpiece can have at least one ingressive end where the optical energy comes into the handpiece, and at least one emissive end where the optical energy leaves the handpiece. During use, the handpiece can be either held steady in order to deliver the optical energy, or can be in motion while the optical energy is delivered.

As previously discussed, the present invention is directed to handpieces which comprise at least one handpiece characteristic data storage system which electronically stores characteristic data. The characteristic data can be characteristic data for the handpiece itself, characteristic data for a set of interchangeable handpieces, characteristic data for at least one optical energy system and/or source, and/or characteristic data for the handpiece in combination with at least one optical energy system and/or source.

Optionally, the devices of the present invention can comprise one or more optical system and/or source characteristic data storage systems. An optical system and/or source characteristic data storage system can store characteristic data for the optical energy system and/or source itself, characteristic data for a set of optical energy systems and/or source, characteristic data for a handpiece in combination with the optical energy system and/or source, characteristic data for a set of handpieces in combination with the optical energy system and/or source, characteristic data for a set of handpieces and/or a set of optical energy systems and/or sources. Similarly, the devices of the present invention can optionally comprise one or more characteristic data storage systems for other components of the device, such as, for example, an optical energy transmission system.

The characteristic data can comprise at least one piece of characteristic data, or can comprise a set consisting of more than one piece of characteristic data. The characteristic data comprises data describing characteristics that have been determined for a particular component and/or for how the particular component functions. The characteristic data can be determined individually for an individual component, can be determined individually for a group of components, can be determined as a group for a group of components at the same time. The characteristic data can additionally comprise a more generic description of a type of component, and/or the specifications for that type of component.

In one example, characteristic data can comprise a description of a beam of optical energy produced by one individual optical energy system and/or source such as, for example, beam diameter, beam pointing error, beam eccentricity, and/or beam wavefront curvature. Characteristic data can comprise descriptions of the functional parameter limits and/or ranges determined for one individual optical energy system and/or source, such as, for example, wavelength range, beam energy density range, transmittance, beam pulse delay range, beam pulse duration range, beam pulse pattern range, scanner speed range, scanner deflection range, scanner settling time, and/or scanner response time. Characteristic data can comprise a more general description of the type of an individual optical energy system and/or source or of the manufacturing specifications for the type of optical energy system and/or source such as, for example, wavelength, wavelength range, wavelength compatibility range, beam energy density range, beam pulse delay range, beam pulse duration range, and/or beam pulse pattern range. This general characteristic data can describe, for example, the wavelength range used to determine whether or not a given type of optical source is within manufacturing specification, as opposed to the individual characteristic data which would describe, for example, the actual ranges of wavelengths produced by an individual optical energy source at one point in time.

In another example, characteristic data can comprise a description of the beam path through optical elements of one individual device component (e.g., an optical energy system, a handpiece, a optical energy delivery system, a transmission system, and/or a characteristic compensation system) such as, for example, transmittance, optical path pointing error, optical path eccentricity, and/or focal length. The characteristic data can comprise general characteristic data about a component, such as, for example, information about the elements that make up the component, and/or about how the component functions, such as, for example, wavelength compatibility range, range of beam diameters, scanner speed range, scanner deflection range, scanner settling time, scanner response time, scanner wheel diameter, number of scanner wheel apertures, lengths of scanner wheel apertures, distances between scanner wheel apertures, number of scanner wheel facets, lengths of scanner wheel facets, width of scanner wheel facets, angles of scanner wheel facets, number of lenses, type of lenses, range of lens positions, number of prisms, type of prisms, range of prism positions, number of mirrors, type of mirrors, and/or range of mirror positions. The characteristic data for an individual component can comprise individual characteristic data and/or general characteristic data.

The characteristic data stored electronically in the characteristic data storage systems of the present invention is used to determine the parameter settings to use to adjust the functional parameters of the components in order to allow the components to operate together properly. The functional parameters for an optical energy source or for an optical energy system comprising an optical energy source can comprise, for example, wavelength (for tunable optical energy sources), beam energy density, duty cycle, transmittance, beam pulse delay, beam pulse duration, beam pulse pattern, scanner speed, lens position, prism position, mirror position, and combinations thereof. The functional parameters for a component which does not produce optical energy such as, for example, a handpiece, an optical energy transmission system, or a characteristic compensation system can comprise, for example, transmittance, scanner speed, lens position, prism position, mirror position, and combinations thereof.

In the drawings, FIG. 1 is composed of two diagrammatic views, FIG. 1A and FIG. 1B, illustrating two examples of handpieces which can be used to deliver optical energy. FIG. 1A shows the basic elements of a handpiece 100 in accordance with the present invention: a handpiece 100 comprising an optical energy delivery system 110 and a handpiece characteristic data storage system 120 electronically storing characteristic data. The handpiece is shown having an ingressive end 145, where optical energy enters the handpiece, and an emissive end 185, where optical energy exits the handpiece. When the handpiece 100 is used to deliver an optical energy based treatment, the beam of optical energy enters the handpiece at its ingressive end 145, passes through the handpiece 100 including the optical energy delivery system 110, and exits the handpiece at the emissive end 185.

The handpiece embodiment of FIG. 1A also shows the path of a beam of optical energy 115 through the handpiece 100 and the optical energy delivery system 110. The handpiece also shows various electronic connections 125 between the components of the handpiece 100 which can be connected to a controller (not shown) so as to allow the controller to control the components, and to access the electronically stored characteristic data. Optionally, the handpiece can comprise an electronic connector 130 which can be configured to be repeatedly connected to, disconnected from, and reconnected to a controller or to another electronic connector. The handpiece can optionally comprise an optical connector 140 which can be configured to be repeatedly connected to, disconnected from, and reconnected to an optical energy system, an optical energy source, an optical energy transmission system, or another optical connector. The electronic connector 130 and/or the optical connector 140 can be configured to allow the handpiece to be used interchangeably with more than one optical energy system and/or source, or for multiple handpieces to be used interchangeably with a single optical source.

The optical energy delivery system 110 is configured to be controlled by a controller. The handpiece characteristic data storage system 120 is configured to be accessed, read, and/or written to by a controller. For example, the controller can electronically record handpiece characteristic data in the handpiece characteristic data system, as well as electronically access stored characteristic data. The controller can also electronically adjust elements of the handpiece, such as the optical energy delivery system, in order for the handpiece to function as part of a device. FIG. 1A illustrates possible electronic connections 125 which would allow the optical energy delivery system 110 and the handpiece characteristic data storage system 120 to communicate with a controller when the handpiece is connected to an optical energy system and/or a controller. The controller which controls the optical energy delivery system 110 and the handpiece characteristic data storage system 120 can be located in the handpiece 100, can be located in another component of the device, or can be free-standing and separate with various electronic connections therebetween.

In one example, the handpiece characteristic data storage system 120 can further comprise a security chip and/or memory. The security chip and/or memory can hold characteristic security data for the handpiece. In this example, the device can be configured to operate only when the handpiece can be authenticated by the controller in order to allow the system to use only authentic handpieces and not counterfeit delivery systems. A unique identification number may be stored to provide further flexibility in preventing counterfeiting. The characteristic data can be encrypted to can include encryption means. This can be particularly useful for characteristic security data in order to make counterfeiting more difficult. In another example, the handpiece characteristic data storage system can comprise a safety system, where the device can be configured to operate only when the handpiece is present and properly attached. In yet another example, the handpiece characteristic data storage system can be used as a handpiece data storage system by storing use data for the handpiece, and can be accessed by a controller in order to ensure the handpiece is calibrated and/or cleaned at pre-determined intervals.

The handpiece 100 can comprise an optical energy beam pathway 115, which can be, for example, one or more optical fibers, lenses, reflective elements, or diffractive or holographic elements. The optical energy pathway 115 in the handpiece 100 can include optics to receive and transmit optical energy from the ingressive end of the handpiece 145 to the ingressive end of the optical energy delivery system 110, and from the emissive end of the optical energy delivery system to the emissive end of the handpiece 185 in order to deliver the optical energy to a target portion of tissue to be treated. The handpiece 100 can comprise a reconnectable optical connector 140.

The handpiece 100 can comprise one or more electrical connections 125 between the handpiece and the controller and/or the optical energy system, with one or more reconnectable electrical connectors 130 at the interface of the handpiece. The electrical connectors 130 are not permanent, but rather are configured such that when the handpiece 100 is mechanically attached to the optical energy system and/or the controller, the electrical connections are reliably created and maintained during use and treatment. For example, contact pads, spring contacts, pogo pins, ball contacts and the like can be used for electrical contacts. The electrical connections create a communications path between the handpiece and the optical energy system and/or the controller. The electrical connections can comprise one or more electrical connections, and can be configured to allow a controller to read from and/or write to the characteristic data storage system via single or multiple electrical connections using various communication protocols.

FIG. 1B illustrates a handpiece 100 which comprises several optional elements in addition to the optical energy delivery system 110 and the handpiece characteristic data storage system 120. FIG. 1B illustrates a handpiece 100 comprising an optional characteristic compensation system 150, which is configured to be controlled by a controller and which can be used to adjust or modify a beam of optical energy and/or adjust its path 115 in order to assist in making the handpiece operate properly with an optical energy system and/or source. The characteristic compensation system 150 is composed of a means for modifying a beam of optical energy and/or a means for adjusting a beam path and can, for example, be composed of one or more scanners, one or more lenses, one or more prisms, one or more reflective surfaces, and/or combinations thereof, and can be located in the path of the beam of optical energy 115 either before or after the beam passes through the optical energy delivery system. Alternatively, the characteristic compensation system 150 can be part of the optical energy delivery system. The characteristic compensation system 150 can be included in the handpiece, as shown in FIG. 1B, or can be part of the optical energy system, the optical energy source, or can be a stand-alone component of the device. An optical energy source, system and/or device can comprise more than one characteristic compensation system 150.

The drawing FIG. 1B also illustrates a handpiece 100 comprising an optional reconnectable tip 160. The tip 160 can be easily connected to, disconnected from, and reconnected repeatedly to a handpiece by the treatment provider. The tip can be cleaned prior to being connected or reconnected to a handpiece. Alternatively, the tip 160 can be disposable. In one example, the tip 160 can comprise a security chip and/or memory 170. The tip security chip and/or memory 170 can be configured to be accessed by a controller. In one example, the device can be configured to operate only when the tip 160 can be authenticated by the controller in order to allow the system to use only authentic tips and not counterfeit tips. In another example, for safety, the device can be configured to operate only when the tip 160 is present and properly attached. Alternatively, the security chip and/or memory 170 can store tip use data, and can be accessed by a controller in order to ensure the tip 160 is replaced and/or cleaned at pre-determined intervals. In embodiments employing a tip 160 attached to the handpiece 100, the tip can include an aperture through which the optical energy from the handpiece passes. The drawing FIG. 1B also illustrates a handpiece 100 comprising an optional roller or contact window 180 which can be placed in contact with the tissue to be treated during a treatment.

The handpiece 100 can further comprise one or more electrical connections to the tip 160. The electrical connection(s) at the interface between the tip 160 and the handpiece 100 are not permanent, but rather are configured so that when a tip 160 is mechanically attached to a handpiece 100, the electrical connections are reliably created and maintained during use and treatment. For example, contact pads, spring contacts, pogo pins, ball contacts and the like can be used for electrical contacts. The tip 160 is configured to have electrical contacts to match those of the handpiece 100, although the tip 160 can have more or less electrical contacts than a given handpiece. The electrical connections create a communications path between the tip 160 and the handpiece 100 and/or a controller.

As a handpiece is typically maneuverable and sized for manipulation by a human hand, the shape of the housing of the handpiece 100 can be designed to provide for a wide range of motion to manipulate the handpiece during treatment. The handpiece housing can be made out of a light plastic. The handpiece can include a heat sink and/or can include a cooling system. The handpiece 100 can contain a structure that allows a beam of optical energy to be guided through the handpiece and to be emitted from a tip 160 attached to the distal end of the handpiece, so that the beam can propagate towards a target portion of tissue. For an efficient treatment, the beam of optical energy can be emitted from the emissive end of the handpiece 185 at a substantially right angle to a target portion of tissue 190.

FIG. 2 is composed of two diagrammatic views illustrating optical energy devices comprising an optical energy system and a handpiece. In FIG. 2A and FIG. 2B, like elements have similar reference numerals to those of FIG. 1A and FIG. 1B. FIGS. 2A and 2B illustrate devices comprising a handpiece 100 and an optical energy system 200 which, when operably coupled, comprise a device such as, for example, an optical energy medical and/or cosmetic treatment system. The handpiece 100 and the optical energy system 200 are reconnectable (i.e., can be connected, disconnected and reconnected repeatedly by a treatment provider). The handpiece comprises an optical energy delivery system 110 and a handpiece characteristic data storage system 120 which stores handpiece characteristic data. The optical energy system 200 comprises an optical energy source 210 and a controller 220 configured to control the optical energy source 210 and the optical energy delivery system 110, and to access the handpiece characteristic data storage system 120. FIG. 2B shows a device comprising an optional reconnectable transmission system 250 for delivering the beam of optical energy from the optical energy system 200 to the handpiece 100. The reconnectable transmission system 250 can include reconnectable optical connectors (140 and 240) at each inlet and outlet, as well as, optionally, reconnectable electronic connectors (130 and 230). The optical energy transmission system can include electronic connections as shown, or the electronic connections 125 can be housed separately. Such connectors can also be wireless.

In other examples, the controller 220 and the optical energy system 200 can be located in separate housings, wherein one or more electronic connections 125 are present between the optical energy system 200 and the controller 220. The controller 220 can comprise a microprocessor and/or a digital signal processor (DSP), as well as software, firmware, algorithms, and/or a look-up table. The controller 220 can be configured to control functional parameters of the optical energy source 210, such as, for example, wavelength (for tunable optical energy sources), beam energy density, duty cycle, beam diameter, beam eccentricity, beam wavefront curvature, beam divergence, beam pulse delay, beam pulse duration, beam pulse pattern, beam pulse pattern repetition rate, scanner speed, wheel speed, lens position, prism position, mirror position, and/or combinations thereof. The controller 220 can be configured to control the characteristic data storage system(s) 120 by electronically recording or storing characteristic data in the characteristic data storage system 120, or by accessing or reading electronically recorded or stored characteristic data in the characteristic data storage system 120. The controller 220 can further assist in the adjustment process by capturing and/or collecting characteristic data, such as during a calibration process, as well as electronically converting or manipulating the characteristic data. The controller can be used to calculate new parameter settings, and to adjust a handpiece 100 and an optical source 210 and/or system 200 so as to function together by implementing new parameter settings, such as source parameters, handpiece parameters, and/or characteristic system parameters. Examples of handpiece and/or source parameters can include beam pulse delay, beam pulse duration, beam pulse pattern, beam pulse pattern repetition rate, scanner speed, wheel speed, lens position, prism position, mirror position, and combinations thereof. In examples where the handpiece 100 optionally further comprises one or more sensors, the controller 220 can be used to control the sensors and to electronically use the data collected by the sensors to alter a treatment parameter or to adjust a handpiece 100 and an optical energy source 210 and/or system 200.

The optical energy source 210 of the optical energy system 200 can comprise a laser, a diode laser, a laser diode array, a flash lamp, or other source of optical energy. When the handpiece 100 and the optical energy system 200 are operably connected, a beam of optical energy can be generated by the optical energy source 210, which is directed out the emissive end of the optical energy source 285, out the emissive end of the optical energy system 295, into the ingressive end of the handpiece 145, through the handpiece 100 and the optical energy delivery system 110, and out the emissive end of the handpiece 185 in order to provide an optical energy based treatment to a portion of tissue.

The optical energy source 210 can be configured to produce one or more beams of optical energy, each having one or more wavelengths. The beam of optical energy can be characterized by a particular set of source parameters that are selected to produce a desired dermatological effect on a target portion of tissue. Source parameters can include optical fluence, beam energy density, beam pulse delay, beam pulse duration, beam pulse pattern, duty cycle, and/or wavelength.

The controller 220 can be used to adjust the handpiece and/or the optical energy source and/or system. The controller 220 can be a general purpose programmable digital computer configured to receive a precise digital output. The controller 220 can be programmed to electronically access handpiece characteristic data stored in the handpiece characteristic data storage system. The controller 220 can be programmed to electronically capture handpiece characteristic data, combined optical energy source/handpiece data, and/or optical source characteristic data. The controller 220 can be programmed to electronically subtract or separate combined optical energy source/handpiece characteristic data into optical source characteristic data and handpiece characteristic data. The controller 220 can be programmed to manipulate the characteristic data or convert the characteristic data so as to transform the data, for example, to convert the data from a time-based value to a distance-based value, or from a distance-based value to a time-based value. Converting data from a distance-based value to a time-based value can be used, for example, to compensate for a beam offset distance by adjusting the delay time of the beam. The controller 220 can be programmed to record or store the handpiece characteristic data in the handpiece characteristic data storage system. The controller 220 can be programmed to use the characteristic data to calculate one or more new parameter settings for the handpiece, for the optical energy system and/or source, and/or for other components of the device. The controller 220 can be programmed to apply logic to determine necessary adjustments for one or more parameter settings that can make the handpiece and the optical energy system and/or source function together, such as, for example, one or more parameter settings that can bring the handpiece and the optical energy system and/or source into alignment with each other. The controller 220 can be programmed to adjust a parameter setting in order to align the optical energy source 210 or system 200 and the handpiece 100 and/or the optical energy delivery system 110.

Additionally, the controller 220 can be used for adjusting in real-time parameter settings in response to detected variations in the handpiece positional parameters, handpiece and/or tip usage, and/or handpiece parameter information. The controller 220 can be programmed to sample in real-time variations in the handpiece positional parameters, usage duration, and/or sensor readings; to display the measurements on a display monitor (not shown); to store the measurements; to apply treatment criteria logic to the measured signals and handpiece/tip information for determining necessary adjustments to parameter settings, and to implement adjustments to at least one parameter setting while the treatment continues. Examples of criteria for treatment logic include changes in the position or the velocity of the handpiece relative to the target portion of tissue, changes in angle of the handpiece relative to the target portion, changes in the distance of the handpiece from the target portion, handpiece and/or tip usage limits, handpiece and/or tip sensor readings, system functional limits imposed by handpiece and/or tip type, handpiece and/or tip treatment parameter limits, handpiece and/or tip usage, and combinations thereof. In some embodiments, separate controllers and processors can be used to control and communicate with the handpiece and/or tip and the positional controls for the optical energy system and/or source.

The controller 220 can further comprise an interface unit (not shown) for receiving and processing signals, analyzing the signals, sending signals requesting determination of suitable parameter settings; and performing adjustments of parameter settings. The interface unit can include analog processing circuitry for normalization or amplification of the signals and an analog to digital converter for conversion of analog signals to digital signals. The interface unit can be operably coupled to the components of the device, i.e., the optical energy source 210, the handpiece 100, the handpiece characteristic data storage system 120, the optical energy delivery system 110, as well as other components of the system, including one or more characteristic compensation systems, one or more security chips and/or memories, one or more detectors or sensors, and/or one or more power supplies.

The controller 220 can further include a processor. The processor can be embodied as a microprocessor, an ASIC, DSP, or other processing means that are suitable. The processor can include computational means for calculating parameter settings, or can be based on neural networks and fuzzy logic techniques for systematically arriving at optimal parameter settings using software in order the components to function together, such as, for example, to align a handpiece and an optical energy source. Alternatively, the computational means can comprise one or more memory look-up tables for generating parameter settings based on characteristic data. Memory look-up tables can provide coherent data sets of characteristic data values and corresponding values of parameter settings. Thus, the software associated with controller 220 allows the processor to perform mapping parameter settings as a function of optical source characteristic data, combined optical source/handpiece characteristic data, and/or handpiece characteristic data.

As discussed previously, the device can further comprise a reconnectable system 250 for delivering a beam of optical energy from the optical energy source 210 and/or optical energy system 200 to the handpiece 100. The system for delivering the beam of optical energy can be repeatedly connected to, disconnected from, and reconnected to the emissive end of the optical energy source 285 or to the emissive end of the optical energy system 295, and the ingressive end of the handpiece 145. The system for delivering a beam of optical energy can be any optical apparatus suitable for transmission of optical energy. Examples of systems for delivering a beam of optical energy include optical fibers and/or articulated arms. The system for delivering a beam of optical energy can be constructed of a material that allows for free manipulation of the handpiece 100 and for repeated bending in order to direct the beam of optical energy to a target portion of tissue to be treated. More than one system 250 for delivering a beam of optical energy can be used to transmit a beam from the optical energy source 210 to a handpiece 100. Optionally, reflective surfaces and/or waveguides can be used to transmit or guide a beam of optical energy.

FIG. 2 also illustrates the electronic connections 125 between the components of the optical energy based medical optical energy system. Within the handpiece 100, electrical connections 125 from the optical energy delivery system 110 and the handpiece characteristic data storage system 120 to the controller 220 are in place when the handpiece is connected to the optical energy system 200. Within the optical energy system 200, a further electrical connection 125 is present between the optical energy source 210 and the controller 220. In this manner, when the handpiece 100 and the optical energy system 200 are connected, the controller 220 can control the optical energy delivery system 110, the handpiece characteristic data storage system 120, and the optical energy source 210.

FIG. 3 is composed of three diagrammatic views, FIG. 3A, FIG. 3B, and FIG. 3C, illustrating three examples of optical energy based devices composed of reconnectable delivery systems and reconnectable optical energy sources. In FIG. 3, like elements have similar reference numerals to those of FIG. 1 and FIG. 2. FIG. 3A illustrates a device composed of a handpiece 100 that can be repeatedly connected to multiple optical energy sources 210a, 210b, 210c and controllers 220a, 220b, 220c housed in separate optical energy systems 200a, 200b, 200c. FIG. 3B illustrates a device composed of a handpiece 100 than can be repeatedly connected to a set of optical energy sources 210d, 210e, 210f and a controller 220 housed in one optical energy system 200. FIG. 3C illustrates a medical optical energy system 200 composed of one optical energy source 210 and controller 220 that can be repeatedly connected to a set of interchangeable delivery systems 100a, 100b, 100c, 100d. One skilled in the art will recognize that two or more optical energy sources (210a, 210b, and/or 210c; 210d, 210e, and/or 210f) can transmit optical energy through one or more optical fibers, and further a single optical energy source 210 can produce multiple wavelengths of optical energy.

FIG. 4 is composed of two drawings, FIG. 4A and FIG. 4B, each illustrating an optimal beam path 415 and two beam paths requiring adjustment (i.e., 117a and 117b, and 117c and 117d) due to an offset in the beam path. In FIG. 4A and FIG. 4B, 415 represents an optimal beam path such as, for example, for a beam exiting the emissive end of an optical energy source, a beam exiting the emissive end of an optical energy system, a beam entering the ingressive end of a handpiece, a beam entering the ingressive end of an optical energy delivery system, or a beam entering the ingressive or emissive end of an optical connector. Beam paths 117a and 117b, as well as 117c and 117d represent two beam paths that would require adjustment in order to align with the optimal beam path 415 or in order to hit a target point 440 at the desired angle.

In FIG. 4A, the beam paths 117a and 117b are parallel to the optimal beam path 415 but are offset from the optimal beam path 415. The offset can be described as a direction (e.g., $d_a$ or $d_b$) and as a magnitude (e.g., $m_a$ or $m_b$). The direction can be described in one dimension (e.g., as positive or negative relative to a reference position), in two dimensions (e.g., using x and y coordinates or using angular measurements), or in three dimensions (e.g., using x, y and z coordinates). The magnitude can be described as a distance. Alternatively, the offset can be described as a combination of a magnitude and a direction. In FIG. 4B, the beam paths 117c and 117d are not parallel to the desired beam path 415 and so are offset from the desired beam path 415 by an angle (e.g., $\theta_c$ or $\theta_d$) that can be described as an angle, or can be described as a direction and/or magnitude, for example, from a point where the possible beam path 117d would hit a target point 440, or using polar coordinates. Beam path 117d is also offset by a direction and magnitude (e.g., $d_d$ and $m_d$), which can be described as discussed above.

For the purposes of the present invention, data describing a pointing error of a beam and/or a possible beam path as described above can comprise characteristic data. In a similar manner, data describing eccentricity of a beam can comprise characteristic data. Data describing beam diameter can comprise characteristic data. Data describing wavefront curvature of a beam can comprise characteristic data. Data describing beam energy density can comprise characteristic data. Data describing other aspects of a beam of optical energy, and/or describing a possible beam path through a component of a device can comprise characteristic Various means known within the art can be used in order to alter beams produced by an optical energy system or optical energy source, and/or to alter possible beam paths 117a, 117b, 117c, or 117d through a component of a device, such as, for example, a beam path through an optical energy source, an optical energy system, a system for delivering a beam of optical energy, a handpiece, an optical energy delivery system within a handpiece, and/or a characteristic compensation system. The means for altering a beam and/or a beam path can be implemented using one or more optical elements, such as, for example, a mirror, a lens, a prism, a reflective surface, a refractive surface, a scanner, a rotating element, a counter-rotating wheel, and/or an electro-optic element, an acousto-optic element.

Figure 5B:
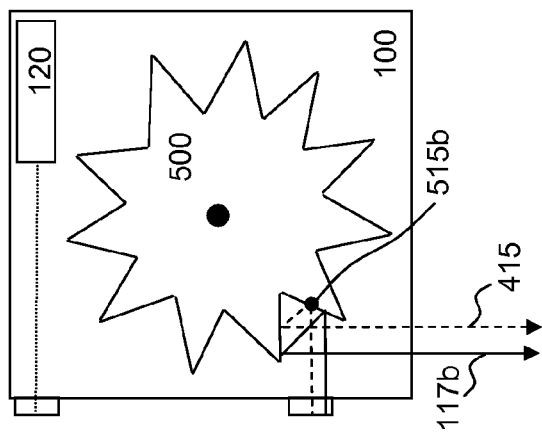
FIG. 5B illustrates the optimal beam path and an actual beam path requiring adjustment.
Figure 5A:
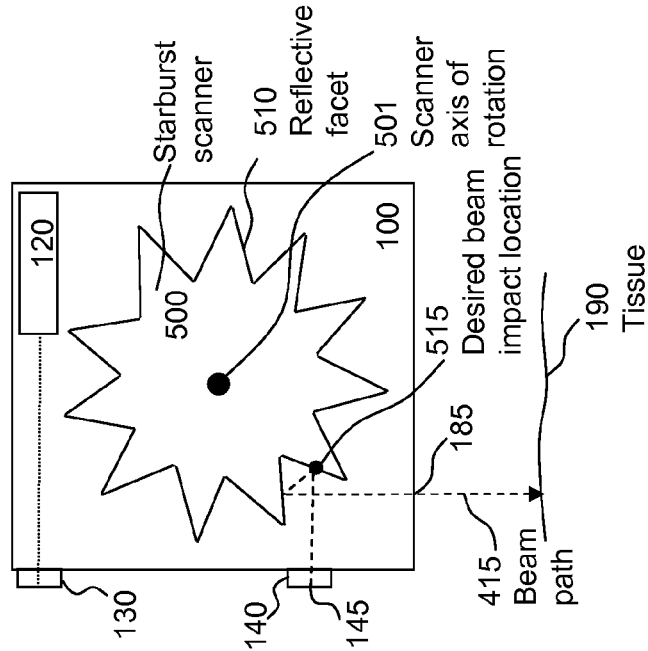
FIG. 5A illustrates an optimal beam path through the handpiece and the optical energy delivery system.

FIG. 5 is composed of three drawings, FIG. 5A, FIG. 5B, and FIG. 5C illustrating diagrammatic views of a handpiece 100 comprising an optical energy delivery system employing a starburst scanner 500, showing an optimal beam path 415 through the handpiece 100 and the optical energy delivery system, as well as an actual beam path before 117b and after 117c adjustment. FIG. 5A illustrates a handpiece 100 comprising a handpiece characteristic data storage system 120 and an optical energy delivery system employing a starburst scanner 500, illustrating an optimal beam path 415 through the handpiece 100 and the optical energy delivery system of the handpiece 500. The handpiece 100 has an electrical connector 130 and an optical connector 140. When properly adjusted and used to deliver a treatment beam to a portion of tissue, a beam of optical energy enters the ingressive end 145 of the handpiece from an optical source and/or system, passes through the optical connector 140, impacts a first reflective facet 510 at an optimal impact location 515, reflects off the first reflective facet 510 of the starburst scanner 500, impacts and reflects off a second reflective facet 510 of the scanner 500, passes out the emissive end 185 of the handpiece, and treats a portion of tissue 190. During use, the starburst scanner 500 rotates around an axis 501 in either a clockwise or counter-clockwise direction at a speed that can be adjusted. The angles of the reflective facets 510 and the number of reflective facts of the scanner 500 determine the position of the beam as it impacts the tissue. The speed of rotation of the scanner 500 and the timing of the beam pulse are set such that beam pulses impact and reflect from the facets 510 as the scanner 500 rotates.

The use of scanners, such as, for example, a starburst scanner 500 or a rotating wheel scanner, can make it necessary that time based parameters (e.g., rotation rates, pulse rates, pulse delays, and/or pulse durations) be taken into consideration in order to adjust the components of the device so they function together. Further, in adjusting the components of such devices, it is possible to use time settings in order to compensate for offsets, such as, for example, direction, magnitude and/or angular offsets. In FIG. 5A, the optimal beam path 415 through the handpiece 100 is shown. FIG. 5B illustrates the path of a beam 117b which is misaligned from the optimal beam path and thus requires adjustment. Beam 117b is parallel to the optimal beam path 415 with an offset that can be described as a negative offset (below the optimal path) of a certain magnitude. The path of the beam 117b does not impact the first reflective facet at the optimal beam impact location 515, but instead impacts it at a different location on the first reflective facet, is then reflected to the second reflective facet and ultimately is offset from the optimal beam path 415 as it is emitted from the handpiece.

FIG. 5C illustrates how a time-based functional parameter of the device can be adjusted to compensate for a beam offset in order to at least partially align a beam path 117b with an optimal beam path 415. This type of timing adjustment can also be used to increase the duty cycle of the scanner by allowing an improved choice for the scanner position during pulsation of the laser beam. For the purposes of this invention, an adjustment of a parameter setting which makes a handpiece and/or other component of a device function in conjunction with the other components of a device can comprise an adjustment which allows a beam to follow an optimal beam path, to follow a portion of an optimal beam path, and/or to impact a desired target location in the device or on the region of tissue undergoing treatment within a pre-determined tolerance. In FIG. 5C, 501b represents the original scanner position (solid lines) at the time the beam 117b is fired, 501c represents the new scanner position (dotted lines) after adjusting the beam pulse delay in order to adjust the position of the starburst scanner at the time the beam is fired and the location on the first facet 515c where the beam impacts the first reflective facet of the scanner 500, and 502 represents the direction in which the scanner can be rotated in order to move from position 501b to 501c, assuming the normal direction of motion of the starburst scanner during operation is in the counter-clockwise direction. In FIG. 5C, beam path 117b represents the path of the beam as the beam is emitted from the handpiece prior to adjustment, and beam path 117c represents the path of the beam as the beam is emitted from the handpiece after the adjustment, which now follows the optimal beam path 415 within the pre-determined tolerance as the beam is emitted from the handpiece. Although the beam path entering the handpiece is below the optimal path, by adjusting the scanner position at the time the beam pulse impacts it, the scanner position has, in effect, been moved so that the optimal impact location 515c is in line with the beam path 117c, which compensates for the offset in the beam path 117c as the beam enters the handpiece, and aligns the beam path 117c with the optimal beam path 415 as it exits the emissive end of the handpiece.

Such an adjustment in the scanner position can be made by adjusting the timing of the beam pulse by calculating the required delay in the beam pulse so that the pulse is not fired until the scanner is in the position 501c which will adjust for the offset of beam 117c as it enters the handpiece. This calculation can be made by the controller based on a stored algorithm using characteristic data such as characteristic data individual for the handpiece or optical source and/or system, or the calculations can have been made in advanced for a number of possible offsets, and the results stored in a look-up table for use at the time of connection.

Parameter settings for use in adjusting other types of scanners and/or other types of optical components can be determined in similar manners, and used similarly in order to compensate for misalignment or offset of a beam and/or beam path by adjusting the timing of a component. For example, calculations can be made which correlate and/or convert a distance offset to a time offset or a time offset to a distance offset in a similar manner. In another example, calculations can be made which correlate and/or convert a distance, magnitude and/or angular offset to a time offset or a time offset to a distance, magnitude and/or angular offset.

As previously discussed, the devices and methods of the present invention employ handpieces which comprise handpiece characteristic data storage systems electronically storing characteristic data. The handpieces of the present invention are configured such that a user or treatment provider can repeatedly connect a handpiece to, disconnect a handpiece from, and/or reconnect a handpiece to at least one optical energy system comprising at least one optical energy source and at least one controller. The handpieces of the present invention can be configured to be interchangeable with other handpieces. The handpieces of the present invention can additionally be used interchangeably with more than one optical energy system and/or source, or can comprise sets of handpieces that can be used interchangeably with one or more optical energy sources and/or systems. When a handpiece of the present invention is connected to an optical energy source and a controller (i.e., an optical energy system), the characteristic data stored in the handpiece characteristic data storage system can be accessed and used to adjust the handpiece with the optical energy source and/or the optical energy system. Once connected and adjusted, the handpiece can be used to deliver optical energy, for example to provide an optical energy based treatment to a tissue such as human skin. One handpiece connected and aligned with at least one optical energy source and/or system which is configured so as to provide a safe and effective medical treatment to a biological tissue will be understood to comprise an optical energy based medical treatment device. The present invention further includes methods for characterizing and electronically storing characteristic data for reconnectable handpieces and optical energy systems and/or sources, and for adjusting reconnectable handpieces and optical energy systems and/or sources.

The handpieces of the present invention can comprise one or more handpiece characteristic data storage systems storing electronic characteristic data, wherein the one or more handpiece characteristic data storage systems are configured to be accessed by a controller. Optionally, the devices of the present invention can comprise one or more optical energy source characteristic data storage systems.

The characteristic data stored in a characteristic data storage system can be used to determine an appropriate parameter setting to use in order to bring a beam and/or a beam path into characteristic with an optimal beam and/or beam path within a pre-determined tolerance. The parameter setting can comprise, for example, a handpiece parameter setting, an optical energy system and/or source parameter setting, an optical energy delivery system parameter setting, a characteristic compensation system parameter setting, and/or a telescope parameter setting. The parameter setting can comprise a functional parameter of the optical energy system and/or source. The functional parameter of the optical energy system and/or source can comprise a time-based parameter setting, such as, for example, a beam pulse delay, a beam pulse duration, a beam pulse pattern repetition rate, and/or a duty cycle. The functional parameter of the optical energy system and/or source can comprise a distance-based parameter setting, such as, for example, a beam diameter, and/or a focal distance. The functional parameter of the optical energy system can comprise an energy-based setting, such as, for example, beam energy density, and/or fluence.

The characteristic data stored electronically on the delivery systems of the present invention can comprise characteristic data for the handpiece itself, including the components of the handpiece, such as the optical energy delivery system. It can comprise characteristic data for any optional components of the handpiece, such as a characteristic compensation system, windows, apertures, optical connections, optical connectors, and/or collimators. The characteristic data can comprise characteristic data for the handpiece in combination with an optical energy system and/or an optical energy source. The characteristic data can comprise characteristic data for the handpiece in combination with a system for delivering a beam of optical energy from an optical energy system and/or source to a handpiece. The characteristic data can comprise characteristic data for an optical energy system and/or an optical energy source by itself. The characteristic data can comprise characteristic data for any optical components of the optical system and/or source, such as, for example, a characteristic compensation system, optical connections, optical connections, and/or collimators. The characteristic data can comprise characteristic data for a system for delivering a beam of optical energy from an optical energy system and/or source to a handpiece. The characteristic data can comprise data for more than one handpiece, system for delivering a beam of optical energy, and/or optical energy system and/or source.

The characteristic data can comprise data describing an functional parameter of a beam of optical energy, such as, for example, a beam energy density, a fluence, a beam pointing error, a beam eccentricity, a beam diameter, a beam wavefront curvature, a beam divergence, a beam waist at a given point, a beam diameter at the focal point, a beam focal distance, a beam pulse delay (i.e., the amount of time elapsed between the end of one pulse and the beginning of the next pulse), a beam pulse duration (i.e., the amount of time elapsed between the beginning and end of one pulse), a beam pulse pattern, a beam pulse pattern repetition rate, and/or combinations thereof.

The characteristic data can comprise data describing one or more deviations of an actual beam of optical energy and/or a beam path from an optimal beam and/or beam path. For example, the characteristic data can describe a deviation in a where the actual beam and/or beam path points as compared to the optimal beam and/or beam path (i.e., a pointing error). The characteristic data can describe the eccentricity of the actual beam and/or beam path as compared to the optimal beam and/or beam path. The characteristic data can describe the beam diameter of the actual beam and/or beam path as compared to the optimal beam and/or beam path. The characteristic data can describe the wavefront curvature of the actual beam and/or beam path as compared to the optimal beam and/or beam path. The characteristic data can describe the angle of the actual beam and/or beam path as compared to the optimal beam and/or beam path. The characteristic data can describe the divergence of the actual beam and/or beam path as compared to the optimal beam and/or beam path. The characteristic data can describe the beam waist at a given point of the actual beam and/or beam path as compared to the optimal beam and/or beam path.

The characteristic data can comprise data describing a pointing error of a beam of optical energy and/or a possible beam path, such as, for example, a beam and/or possible beam path within a handpiece, within a system for delivering a beam of optical energy that is part of a handpiece, within an optical energy system and/or source, and within a combination thereof. The pointing error can be described as a direction, as a direction and a distance, as an angle, as a direction and an angle, or as a distance and an angle. The pointing error can be described in one or two dimensions. The pointing error can be described as an offset and/or as an adjustment that corrects for the offset. The pointing error can be described in terms of a distance-based value, or in terms of a time-based value. The pointing error can be compensated for by altering all of, or a portion of a beam and/or beam path. The pointing error can be compensated for by altering a beam and/or beam path using optical elements such as, for example, one or more lenses, prisms, mirrors, and/or rotating reflective surfaces. The pointing error can be compensated for by adjusting optical elements within the handpiece and/or the optical energy system and/or source, or by adjusting optical elements in a characteristic compensation system. The pointing error can be compensated for by altering a timing parameter of the beam and/or a component of the device, such as, for example, beam pulse delay, beam pulse duration, and/or scanner speed.

The characteristic data can comprise data describing eccentricity of a beam of optical energy and/or a possible beam path. The eccentricity can be described as a direction and/or a magnitude. The eccentricity can be described in one or two dimensions. The eccentricity can be described as an offset and/or as an adjustment that corrects for the offset. The eccentricity can be described in terms of a distance-based value, or in terms of a time-based value. The eccentricity can be compensated for by altering a beam and/or beam path using optical elements such as, for example, one or more lenses, prisms, mirrors, and/or rotating reflective surfaces. The eccentricity can be compensated for by adjusting optical elements within the handpiece and/or the optical energy system and/or source, or by adjusting optical elements in a characteristic compensation system. The eccentricity can be compensated for by altering a timing parameter of the beam and/or a component of the device, such as, for example, beam pulse delay, beam pulse duration, and/or scanner speed.

The characteristic data can comprise data describing beam diameter of a beam of optical energy and/or of a possible beam path. The beam diameter can be described as a distance. The beam diameter can be described in one or more dimensions, depending upon the shape of the beam. The beam diameter can be compensated for by altering all of or a portion of a beam path. The beam diameter can be compensated for by altering a beam and/or beam path using optical elements such as, for example, one or more lenses, prisms, mirrors, and/or rotating reflective surfaces. The beam diameter can be compensated for by adjusting optical elements within the handpiece and/or the optical energy system and/or source, or by adjusting optical elements in a characteristic compensation system. The beam diameter can be compensated for by altering the beam focal point.

The characteristic data can comprise data describing wavefront curvature of a beam of optical energy and/or a possible beam path. The wavefront curvature can be described as positive or negative. The wavefront curvature can be compensated for by altering all of or a portion of a beam and/or beam path. The wavefront curvature can be compensated for by altering a beam and/or beam path using optical elements such as, for example, one or more lenses, prisms, mirrors, and/or rotating reflective surfaces. The wavefront curvature can be compensated for by adjusting optical elements within the handpiece and/or the optical energy system and/or source, or by adjusting optical elements in a characteristic compensation system.

The characteristic data can comprise a positional parameter or positional data of a moving component of a handpiece, an optical energy delivery system, a characteristic compensation system, and/or an optical energy system and/or source. The positional parameter or positional data can comprise, for example, a mirror position, a lens position, a prism position, a position of an assembly of elements, such as, for example, a telescope position. The positional parameter or positional data can be described in one or two dimensions.

The characteristic data can comprise a timing parameter of a moving component of a handpiece, an optical energy delivery system, a characteristic compensation system, and/or an optical energy system and/or source. The moving components can comprise a moving or rotating optical element such as, for example, a galvanometer scanner and/or a starburst scanner. The timing parameter can comprise, for example, a scanner speed and/or a wheel speed.

In the example where the optical energy delivery system comprises a starburst scanner, the characteristic data can comprise data specific to the type of starburst scanner housed in a handpiece, or data specific to an individual starburst scanner housed in a handpiece. The characteristic data can comprise, for example, a range of compatible wavelengths, a wheel diameter, a wheel speed, a number of apertures on the wheel, a number of facets on the wheel, a width of a facet, a length of a facet, the location of a desired target impact area on a facet, a distance between each aperture on the wheel, an angle of each facet on the wheel, a time duration from one aperture to the next aperture on the wheel for a given rotation speed, a time delay to use for a given beam pointing error and/or eccentricity based on a given rotation speed, and/or a time delay to use for starting a beam pulse relative to an index point at a given rotation speed.

As previously discussed, the characteristic data stored electronically in the characteristic data storage systems of the present invention is used to determine the parameter settings that can be used in order to adjust the functional parameters of the components in order to allow the components to operate together, or can comprise the parameter settings themselves.

Thus, the characteristic data stored in characteristic data storage systems of the present invention is used not merely used to "identify" or "decode" the handpieces or components to enable the device to "recognize" the handpieces and/or components. The characteristic data of the present invention can be used both to identify handpieces and other components, and to adjust handpieces and other components.

In one embodiment of the device of the present invention, the controller can be configured to read and/or access characteristic data stored in a handpiece characteristic data storage system and to determine one or more parameter settings for the device based on the stored characteristic data. Determining one or more parameter settings for the device based on the stored characteristic data can comprise electronically performing calculations using the stored characteristic data, manipulating the stored characteristic data, converting the stored characteristic data, correlating the characteristic data with pre-determined parameter settings, and/or using a look-up table to determine parameter settings. Determining one or more parameter settings based on the stored characteristic data can comprise separating combined optical energy source/handpiece characteristic data into handpiece characteristic data and/or optical energy source characteristic data. Determining one or more parameter settings based on the stored characteristic data can comprise converting data from a time domain to a distance domain and/or from a distance domain to a time domain.

In another embodiment, the controller can be configured to adjust and/or move one or more elements or components of the device in order to implement the one or more parameter settings discussed above. In another embodiment of the device, the controller can be configured to electronically collect and/or capture characteristic data (e.g., handpiece characteristic data, combined optical energy source/handpiece characteristic data, and/or optical energy source characteristic data). In yet another embodiment, the controller can be configured to electronically record and/or store characteristic data in memory (e.g., a handpiece characteristic data storage system, and/or a source characteristic data storage system.)

In one embodiment, the controller can be configured to adjust and/or move one or more elements or components of the device in order to implement a parameter setting which will bring a beam and/or beam path into alignment with an optimal beam and/or beam path within a pre-determined tolerance.

The parameter setting can comprise a parameter setting of an optical element of a handpiece, an optical energy delivery system located in the handpiece, a transmission system, and/or a characteristic compensation system. The parameter setting of an optical element can comprise the position of a movable part, such as, for example, a lens position, a prism position, a mirror position, a telescope position, etc, and can comprise a description of the position in one or two dimensions. The parameter setting can comprise a parameter setting of a moving part, such as, for example, a scanner and/or wheel that is rotated while in use. The parameter setting of a moving part can comprise a setting such as, for example, a scanner speed, a wheel speed, and/or a delay time relative to an index point on a rotating element. In the example where the scanner comprises a starburst scanner, the parameter setting for the scanner can comprise a rotation speed to use in order to align a beam and/or beam path, and/or a delay time to use relative to an index point in order to align a beam and/or a beam path.

In one embodiment, when the optical delivery system of the handpiece comprises an optical scanner, the controller can be configured to adjust the at least one optical energy source and/or the optical scanner or an optical component so that a deviation in direction, distance and/or angle of a beam path of the beam of optical energy is compensated for by implementing a beam pulse delay time, wherein implementing the beam pulse delay time results in alignment of the beam pulse with an index point and/or an optimal impact point on a facet as the scanner is rotated. For example, if the beam is offset such that the actual beam and/or beam path impacts a facet at a point that was past an optimal point, the beam pulse delay can serve to align the beam and/or beam path by delaying the firing of the beam pulse until another facet has rotated and is in position. This type of delay serves to displace the actual beam and/or beam path along the line of motion of the scanner in the positive direction of motion of the scanner.

The characteristic data storage system of the present invention, including the handpiece characteristic data storage system, can comprise a chip and/or a memory configured to be accessed by a controller. The handpiece characteristic data storage system can be attached directly or indirectly to the handpiece. The handpiece characteristic data storage system can comprise memory such as, for example, an EPROM or an EEPROM. The handpiece characteristic data storage system can be a separate and stand-alone memory element, or can be part of another component, such as, for example, a security chip, a control chip, a processor, and/or a microprocessor. The handpiece characteristic data storage system can be located within the handpiece, or can be located outside the handpiece. The handpiece characteristic data storage system can comprise one or more electrical connectors in order to form an electrical connection with a controller. The electrical connectors are be configured to be repeatedly connected, disconnected and/or reconnected by a user in order for the handpiece to be repeatedly connected, disconnected and/or reconnected to an optical energy source and/or system. Within the handpiece, the handpiece characteristic data storage system can optionally be connected via one or more electrical connections to other components of the handpiece, such as, for example, the optical energy delivery system, a characteristic compensation system, a tip, and/or a security chip and/or memory. The electrical connections can comprise wires, electrical contacts, and the like.

As previously discussed, the characteristic data of the present invention can also serve a security purpose, to ensure that only authentic, authorized, approved and/or specified handpieces are used with in conjunction with approved and/or specified optical energy systems and/or sources. The handpiece characteristic data storage system can thus additionally serve as a handpiece security system. A handpiece security system can consist of a memory holding a secure and/or encrypted code (e.g., a hash algorithm, for example a 128-bit Secure Hash Algorithm-1 (SHA-1) codes) for use in authenticating a handpiece to an optical energy system. In this example, the optical energy system can include a controller and a memory holding a similar or matching code to that is stored in handpiece memory, such as in the handpiece characteristic data storage system. One or more encryption algorithms, handshake protocols, and/or authentication procedures can be used to ensure that an authentic handpiece is used with the system. For example, a Dallas Semiconductor DS2432 1 k-Bit Protected 1-Wire™ EEPROM (manufactured by Dallas Semiconductor of Sunnyvale, Calif.) can be used for such secure and encrypted memory. In this example, a single wire can be used between the memory and the controller and/or handpiece characteristic data storage system and communication can be completed by a 1-wire protocol (e.g., 1-wire SHA-1 protocols).

As previously discussed, in some embodiments, information relating to the usage of the handpiece can be stored in the handpiece characteristic data storage system, and the handpiece characteristic data storage system can be used to monitor and/or control handpiece usage. Handpiece usage data can comprise, for example, an accumulated time of use; a clock time since a tip was attached to the handpiece, since the handpiece was calibrated, and/or since the optical energy system was first turned on with the handpiece and/or tip attached; a number of pulses transmitted through the handpiece and/or tip; an accumulated energy or fluence transmitted through the handpiece and/or tip; a number of patients treated using the handpiece and/or tip; a number of treatment spots laid down through the handpiece and/or tip; and/or combinations thereof. A usage limit based on handpiece usage data can be stored in the handpiece characteristic data storage system such that when the usage limit is exceeded, the handpiece and/or the system cease to function in part or in whole. The implementation of a usage limit can allow a calibration schedule to be enforced, which can, when the system is used to deliver a treatment to a patient, help ensure a safe and efficacious treatment is provided.

Additionally, other handpiece usage parameters and/or handpiece component usage parameters gathered during treatment with the handpiece can be stored in the handpiece characteristic data storage system, such as, for example: pulse delay; pulse duration; wavelength(s); number of sources used; temperature of the treatment area, handpiece and/or system; number of patients treated; and/or types of treatment regimens used (for example, multiple pass treatments or single pass treatments). These other handpiece usage parameters can be useful in determining handpiece life and/or for adjusting treatment parameters over the life of the handpiece, for example. If the handpiece is removed from a system and later coupled to the same or a different system, these saved parameters can be useful in monitoring total handpiece life and/or in setting appropriate treatment parameters taking into account the history of the handpiece.

Further embodiments of the present invention can include storing in the characteristic data storage system a code that unlocks a memory in an optical energy system. The unlocked portion of optical energy system memory can store information regarding the specific handpiece-system and/or handpiece component-system combination. For example, a handpiece can store a code relating to a patient or a prior treatment. When such a handpiece is attached to an optical energy system and the handpiece memory is read, the code in the handpiece memory can unlock a section of system memory and patient information or prior treatment parameters are retrieved for use in the current treatment.

As previously discussed, the handpieces of the present invention comprise an optical energy delivery system. The optical energy delivery system is used to direct optical energy at a target. The optical energy delivery system can be configured to direct optical energy at a target portion of tissue. In some examples, the optical energy delivery system can direct a beam of optical energy to a target portion of tissue by directing, focusing or collimating the beam(s) of optical energy to one or more treatment zones within a target portion of tissue. The optical energy delivery system can be implemented using one or more optical elements, such as mirrors, optical lenses, reflector mechanisms, scanner mechanisms, optical windows, rotating elements, counter-rotating wheel elements, electro-optic elements, and/or acousto-optic elements.

The optical energy delivery system can comprise one or more deflector and/or scanner mechanisms. The deflector can be an optical component suitable for deflecting one or more beams of optical energy of a wavelength pre-selected for a treatment, such as, for example, mirrors, prisms, telescopes, grids, diffractive optical elements, holographic elements, and/or rotating elements. A deflector can be used to modify the optical energy beam emitted from an optical energy source and/or from an optical energy system. In one example, a deflector can be movably mounted within a handpiece for displacement of a beam of optical energy in response to a controlling signal from a controller. The optical energy delivery system can include an actuator, such as, for example, a piezoelectric mechanism, a galvanometer, and/or a rotating element, which operates to adjust the position of a deflector to a position corresponding to a desired treatment intensity and/or pattern. The actuator can be controlled in real-time by a controller to modify a beam of optical energy so that a treatment is delivered from the handpiece in a uniform or non-uniform pattern across a target portion of tissue. In some embodiments, additional deflectors, scanners and/or actuators can be used in addition to the optical energy delivery system, in a characteristic compensation system, in a handpiece, in an optical energy system and/or source, in a characteristic compensation system, and/or in combinations thereof.

The optical energy delivery system can comprise an optical scanner. Examples of optical scanners include starburst scanners, galvanometer scanners, rotating wheel scanners, and combinations thereof. U.S. Pat. No. 7,184,184, issued on Feb. 27, 2007, assigned to Reliant Technologies, Inc. and entitled "High speed, high efficiency optical pattern generator using rotating optical elements", describes examples of optical pattern generators comprised of one or more multi-faceted rotating elements, also known as rotating wheel scanners, and includes counter-rotating disk scanners that introduce an offset that is rotation insensitive, and their uses. U.S. Pat. No. 7,196,831, issued on Mar. 27, 2007, assigned to Reliant Technologies, Inc., and entitled "Two-Dimensional Optical Scan System Using a Counter-Rotating Disk Scanner" describes further examples of counter-rotating wheel scanners for creating two dimensional patterns. U.S. application Ser. No. 11/158,907, filed on Jun. 20, 2005, assigned to Reliant Technologies, Inc. and entitled "Optical Pattern Generator Using a Single Rotating Component" describes starburst scanners. The above patents and application are incorporated herein by reference in their entireties.

As previously discussed, the handpieces of the present invention can be configured to be interchangeable, so as to allow the handpieces to be used with one or more optical energy system and/or source, or a set of handpieces to be used interchangeably with one or more optical energy system and/or source. By using device components (e.g., optical energy systems and/or sources, handpieces, controllers, and/or transmission systems) that can be repeatedly connected, disconnected, reconnected and adjusted, cost and complexity of the device can be reduced while providing a variety of effective treatment parameters from a single set of optical energy sources and/or handpieces. In one example, the device can comprise a set of interchangeable components, such as, for example, a set of interchangeable optical energy systems and/or sources and a set of interchangeable handpieces, each with its own optical energy delivery system and handpiece characteristic data storage system. The handpieces of the present invention can further be configured to be interchangeable with tips or rollers, so as to allow the handpieces to be used with more than one type of tip or roller, or a set of tips or rollers, or for a set of handpieces to be used interchangeably with one or more tips or rollers.

As the handpieces of the present invention which store characteristic data are reconnectable, it is possible to change functional parameters and treatment parameters by changing handpieces. For example, different handpieces can have different dimensions along the optical axis of the emissive end in order to alter the focal depth of the treatment beam into the tissue and/or the spot size of the treatment beam at the tissue surface. Different handpieces can deliver the beam in different patterns. Different handpieces can have different sizes in dimensions other than those parallel to the optical axis of the treatment beam. Different handpieces can also have different shapes. Different handpieces can be sized and shaped to treat specific conditions or specific anatomical structures. Different handpieces can have different filter properties in order to limit the wavelength(s) of the optical energy transmitted through the handpieces. Different handpieces can comprise different detectors and/or sensors in order to treat different targets or to provide different types of treatments.

The shape of a handpiece and/or handpiece component (e.g., a tip, roller, window) can be designed to fit particular anatomical areas, such as for example, small or difficult to reach areas around an eye or a nose. For such handpieces, parameter limits can define the functional parameters within which the handpiece can safely and/or effectively be used. Such parameter limits can include, for example: energy limits, wavelength(s), pulse duration(s), beam energy density, temperature limits, contacting versus non-contacting treatments, accumulated time of treatment, and so forth. Characteristic data can define the treatment parameters to be used when employing a particular handpiece and/or handpiece component. For example, characteristic data can indicate that a handpiece be used only with optical energy of a particular wavelength, or at a particular beam energy density setting or fluence. Characteristic data can indicate that a particular dye or contrast agent be used to enhance the sensing response from an LED within the handpiece and/or tip. Additionally, characteristic data can indicate that the handpiece and/or handpiece component is intended for a particular use, such as, around the eyes and nose, or for treating a particular disease or condition, and the intended use of the handpiece can be displayed on a user interface screen to help ensure the treatment provider is using the correct handpiece for the correct purpose, helping to ensure the patient receives a safe and efficacious treatment.

As previously discussed, in another embodiment, the handpiece of the present invention can comprise a set of interchangeable handpieces, wherein each handpiece in the set comprises its own optical energy delivery system and handpiece characteristic data storage system. In one example, each handpiece in a set is individually characterized in order to determine its characteristic data. In another example, the handpiece characteristic data for each handpiece in a set is individually recorded in the handpiece's handpiece characteristic data storage system. In another example, each of the interchangeable handpieces in a set can be configured to deliver optical energy in a different pattern or spot size. Each interchangeable handpiece in the set can be configured to delivery optical energy to a specific anatomical area, in a manner appropriate for treating a specific disease or condition in tissue, or in a manner appropriate for treating a specific target in tissue. Additionally, one or a set of handpieces can be configured to accept a set of interchangeable tips which can be similarly configured to deliver optical energy in a specific pattern, spot size, to a specific anatomical area, in a manner appropriate for treating a specific disease or condition in tissue, and/or in a manner appropriate for treating a specific target in tissue.

For example, individual handpieces and/or tips in a set or plurality of handpieces and/or tips configured to be attached to a single device can be designed for specific purposes such as, for example: treatment of wrinkles, scars, pigmented lesions, tightening of tissue, hair removal or growth; drug delivery; absorption of cosmetic formulations; treatments around eyes, neck, and/or nose; and/or targeting of anatomical structures, such as veins or lesions. A user interface attached to the device can allow a treatment provider to obtain information relating to the handpiece and/or tip as well as information relating to a given handpiece's and/or tip's impact on the device configuration and treatment parameters. A treatment provider can then alter parameter settings and/or switch handpieces and/or tips to achieve the desired treatment.

Various handpiece and/or tip dimensions can be changed between the individual handpieces and/or tips in a set. A set of two or more handpiece and/or tips can be configured to fit and be attached to a given device. Each individual handpiece and/or tip in the set can be different in at least one aspect from the other handpieces and/or tips in the set. The differences between delivery systems and/or tips can include differences in: dimensions; shapes; windows; filters; memory configurations or sizes; number and type of detectors and/or sensors; aperture(s); additional connector mechanisms; number and type of electrical connections; additional sensors; security codes, functional parameters and/or other information stored in handpiece and/or tip memory; and so forth. For example, some of the dimensions that can be different between handpieces and/or tips in a set include the width, which can be different from one handpiece and/or tip to the next. Additionally, window width(s) can be different from one handpiece and/or tip to the next. Altering treatment window width can also impact the aperture of the handpiece and/or tip for treatment purposes. The length can also be different from one handpiece and/or tip to the next. Altering length will typically alter the focal depth of a treatment beam relative to the treatment window and the surface of tissue being treated, as well as the spot size of the treatment beam at the tissue surface.

Altering a length dimension for two tips each attached separately at different times to the same handpiece and optical energy system can result in different treatment characteristics. A handpiece (e.g., in the absence of a tip) can deliver a treatment beam having a set focal length, numerical aperture and beam profile. Two tips, each of different lengths can be attached to the handpiece. This difference in tip length can alter the depth in the tissue at which the beam is focused and will also impact the spot size at the tissue surface. Altering spot size, spot shape and/or focal depth from one tip to another significantly impacts the treatment parameters and typically the tissue response. For example, a larger spot size can cause a larger treatment zone lesion, and a deeper focal point can cause a deeper treatment zone lesion and/or necrotic zone. Further, altering these treatment dimensions can alter the shape and size of the treatment zone.

In another embodiment, the handpiece can further comprise at least one characteristic compensation system configured to be controlled by a controller. The characteristic compensation system is a system that can be adjusted by the controller as needed in order to alter the beam path or to direct, focus or collimate the beam of optical energy in order to adjust a handpiece to function with an optical energy source. The characteristic compensation system can be implemented using one or more optical elements, such as, for example, mirrors, optical lenses, reflector mechanisms, scanner mechanisms, optical windows, rotating elements, counter-rotating wheel elements, electro-optic elements, and/or acousto-optic elements.

In another embodiment, one or more handpieces of a set can further comprise at least one detector and/or sensor. The detector and/or sensor can comprise a detector or sensor selected from the group consisting of a temperature sensor, an optical sensor, a color sensor, an energy diffraction sensor, an energy absorption sensor, an energy scattering sensor, a wavelength sensor, a capacitance sensor, a sensor configured to detect the presence of a particular molecule, a sensor configured to detect the presence of a tissue, a sensor configured to detect contact between the handpiece and a tissue, a sensor configured to detect a tissue characteristic, a sensor configured to detect a tissue response, an optical mouse, a mechanical mouse, an accelerometer, a positional sensor, a magnetic field sensor, an imaging sensor, and combinations thereof. The handpiece and/or optical energy system can be configured to deliver optical energy when a pre-selected condition is detected in the tissue. For example, an imaging sensor can be used to actively target a desired structure or feature in the tissue, such as, for example, pigmented lesions, vascular lesions, hair follicles, combinations thereof.

In yet another embodiment, one or more handpieces of a set can include a detector and/or sensor for detecting variations in the positional parameters of the handpiece. The detector can comprise an image acquiring sensor for repeatedly capturing images of the target portion of tissue and an image processing device for analyzing in real-time varying positional parameters of the handpiece as it is motion. The detector or sensor can be an optical navigation device that allows quantitative measurement of the movement of the handpiece. In an optical navigation device, an optical energy source such as a light-emitting diode illuminates the surface of the tissue underneath a handpiece. The optical energy impacts on the surface to be treated and reflects off the microscopic textural features on the surface. The optical energy can be converged by means of a converging lens. The converged beam of optical energy scattered from the surface can then be refocused by a converging lens to form an image on a position sensor. A sensor can continuously take pictures of the points in the target portion of tissue at high speed as the handpiece is moved. The image capturing speed of the sensor can be sufficiently high to allow sequential pictures to overlap. Sequential images from the sensor can be sent to an image processing device. The optical path of the sensor between the target portion of tissue and the converging lens can include an optically transparent window. The image processing device can be a programmable digital computer that uses an optical navigation engine for analyzing the sequential images captured by the sensor.

An example of a detector usable in a handpiece is an optical navigation sensor produced by Agilent Technologies, Inc., of Palo Alto, Calif., U.S.A., including the ADNS 2600 series optical navigation engine. The optical navigation engine produces measurements of changes in the handpiece position by optically acquiring sequential surface images up to about 1500 times per second and mathematically determining the direction and magnitude of the handpiece movement at the maximum of 400 counts per inch (cpi) and at speeds up to 12 inches per second (ips).

If an optical navigation sensor such as described in the previous paragraph is used in a handpiece, then in some cases this detector or sensor can be made more robust by the addition of one or more contrast-enhancing substances, such as, for example, particles, dyes, solutions, colloids or suspensions, to the target portion of tissue in order to enhance the contrast for the optical navigation sensor. One example of contrast enhancing particles is ink particles that can be spread onto the skin by painting or marking the skin prior to treatment with the handpiece. Food dyes can alternately be used for contrast enhancement. The contrast-enhancing substance can be chosen as an absorber or a reflector of the optical energy used by a detector and/or sensor (e.g., a blue dye can be chosen for use with a red LED).

Further embodiments of the handpiece of the present invention can optionally include a window through which optical energy is transmitted. The window can be a contact window (i.e., a window with is placed in contact with tissue during the treatment process) or a non-contact window. The window can be located within the handpiece and/or within a tip that can be attached to the handpiece. The window can be a treatment window through which optical energy emitted from the system is transmitted to a tissue surface. The window and the treatment window can be a single window in some embodiments. Windows are typically made of glass, sapphire, diamond, quartz or silica, although other substances can be chosen for their optical and/or thermal properties. In some embodiments, windows can include filters for limiting the transmission of one or more wavelengths. For example, in systems having multiple lasers or optical energy sources emitting multiple wavelengths, a handpiece and/or tip can be chosen to transmit or block one or more wavelengths depending on the desired treatment. Such filters can include thin film filters, reflectors and/or coatings in single-layer or multi-layer configurations. Such filters can be absorptive, reflective, or a combination thereof. Such filters can include, for example, doped glass filters, fused silica with a dielectric coating, or silicon. Alternately, windows can include diffractive elements, holographic elements, polarizing elements, opto-electronic elements, acousto-optic elements, a lens, an optical limiter, a saturable absorber, or a passive q-switch element to alter the optical energy transmitted through the window and/or to alter the treatment pattern and spot dimensions on the tissue.

Further embodiments of the handpiece of the present invention can optionally comprise at least one roller configured to contact a tissue to be treated. The roller can be used to guide the handpiece over the tissue during treatment. The roller can be used as part of a motion sensor to ensure that the handpiece is in motion during treatment. Feedback from the roller can thus be used to determine whether or not the handpiece is in motion, can be used to determine whether or not to emit optical energy from the system, and/or can be used to adjust treatment parameters such as treatment zone density, fluence, and/or treatment pattern, based on the feedback.

In another embodiment of the handpiece of the present invention, the handpiece can optionally comprise an interchangeable tip. The tip can be used as the portion of the handpiece that delivers the optical energy directly to the portion of tissue to be treated, either in a contact mode or a non-contact mode. The tip can further comprise optional components such as windows, apertures and/or rollers.

Embodiments of the handpiece of the present invention can optionally further comprise an aperture in the handpiece and/or tip. An aperture can be used to limit the numerical aperture of the system and/or to limit the size of the treatment pattern at the tissue. For example, if the handpiece produces a set number of spots (e.g. 30 across a single line perpendicular to the direction of movement of the handpiece) in a given treatment pattern to create a set treatment zone dimension (i.e. 15 mm wide), then an aperture can be used with a smaller dimensioned tip to limit the treatment to fewer spots and a narrower treatment zone (e.g., 15 spots across an 8-mm-wide line). An aperture can include a reflective coating to direct optical energy ingressive thereon in a desired direction, such as, for example, to a beam dump or an absorbing heat sink. Alternately, an aperture can be a heat sink or an absorber.

In further embodiments of the present invention, when the handpiece comprises a tip, the tip can further comprise a tip security chip and/or memory. The tip security chip and/or memory can be configured to be controlled by the controller of an optical energy system. The tip security chip and/or memory can be configured to be accessed by a characteristic data storage system. The tip security chip and/or memory can store tip configuration information that can be accessed by the controller. In one example, the tip configuration information can be used in the adjustment process. This tip configuration information can include, for example: tip width (e.g., tip treatment zone width and/or length); tip focal properties, such as focal length (in air or in tissue) and spot size (typically measured at the tissue surface); tip shape; tip parameter limits; and/or tip treatment parameters. The tip shape can include, for example, cross-sectional (i.e. at the treatment end of the tip in a plane perpendicular to the optical axis of the treatment beam and/or parallel to the tissue surface) shapes (e.g., round, oval, polygonal, symmetrical or asymmetrical) or profile (i.e. looking at the tip in a direction substantially perpendicular to the optical axis of a treatment beam transmitted through the tip) shapes typically on the treatment facing side(s) of the tip (e.g., flat faced, rounded, polygonal, indented, and/or bumped).

Similarly to the handpiece, the tip shape can also be designed to fit particular anatomical areas, such as for example, small or difficult to reach areas around an eye or a nose. Tip parameter limits can define system parameters within which the tip can safely and/or effectively be used. Such parameter limits can include, for example: energy limits, wavelength(s), pulse duration(s), beam energy density, temperature limits, contacting versus non-contacting treatments, accumulated time of treatment, and so forth. Tip treatment parameters can define treatment parameters to be used when employing a particular tip. For example, tip treatment parameters can include data requiring that a tip be used only with optical energy of a particular wavelength, or at a particular beam energy density setting or fluence. Tip treatment parameters can indicate that a particular dye or contrast agent be used to enhance the sensing response from an LED within the tip or handpiece. Additionally, tip treatment parameters can indicate that the tip is intended for a particular use, such as around the eyes and nose, or for treating a particular disease or condition, and the intended use of the tip can be displayed on a user interface screen to help ensure the treatment provider is using the correct tip for the correct purpose.

It is possible to vary tip width (e.g., tip treatment zone width and/or length); tip focal properties, such as focal length (in air or in tissue) and spot size (typically measured at the tissue surface); tip shape; tip parameter limits; tip treatment parameters; and so forth. The tip shape can include, for example, cross-sectional (i.e. at the treatment end of the tip in a plane perpendicular to the optical axis of the treatment beam and/or parallel to the tissue surface) shapes (e.g., round, oval, polygonal, symmetrical or asymmetrical) or profile (i.e. looking at the tip in a direction substantially perpendicular to the optical axis of a treatment beam transmitted through the tip) shapes typically on the treatment facing side(s) of the tip (e.g., flat faced, rounded, polygonal, indented, and/or bumped).

The tip can include a connector mechanism for attaching the tip to a handpiece. The proximal end of the tip can include a connector mechanism configured to hold the tip in place against the distal end of the handpiece with sufficient force to maintain an electrical contact and an optical coupling between the tip and the handpiece, especially while the handpiece is moved across tissue during treatment. The connector mechanism can take various forms such as, for example, a magnetic connector. Magnets can be placed on one or both sides of the interface between the tip and the handpiece. Alternate attachment mechanisms can include, for example: a clip; a screw; a screw-on connection (i.e. the tip and the handpiece have corresponding male and female threaded portions); an adhesive; a bayonet-style connector; a snap and/or a latch. Additionally, the tip can be shaped so that it can be removably attached to the handpiece. Dowels and corresponding holes can be used to seat and hold the tip against the handpiece. Further, the shape of the tip can be configured to fit the handpiece tightly. For example, the tip shape can be more conformal to match the shape of the distal end of the handpiece, rather than being a flat surface that butts flush against a flat surface of the handpiece.

The tip can further comprise one or more sensors for monitoring various parameters of the tip, optical energy beam and/or the tissue being treated. For example, a monitor photodiode can be included in the tip to monitor the optical energy beam. This can require a partially reflective element to monitor a portion of the treatment beam. This real-time monitoring of treatment beam characteristics can be used to alter the system and/or treatment parameters. A temperature sensor, such as, for example, a thermocouple, can be coupled to the tip. In some embodiments, a thermocouple is attached to the tip at or near the treatment end of the tip, so as to monitor tissue surface temperature. Such sensors are typically in communication with the optical energy system, either electrically, optically or by wireless connection. Further, some embodiments can include radio-frequency identification (RF ID) chips as a further security measure (i.e. if a RF ID communication system is included in the system to check the RF ID on the tip) and for tracking purposes to identify individual chips and their locations relative to the system. Such RF ID chips can store some of the data and codes described above as stored in the handpiece characteristic data storage system.

A controller can read the tip configuration information, tip usage information, tip usage parameters and/or other system information from the tip memory and use software and/or firmware algorithms to create one or more control signal(s) to adjust parameter settings in order to alter the configuration of the optical energy source, optical energy system and/or handpiece. Further, the controller can cause signals to be sent to an interface unit to provide information to a treatment provider. The treatment provider can then make treatment decisions or adjust the functional parameters based thereon, for example, through a touch screen, a keyboard, a mouse or other input mechanism. For example, a handpiece can store information indicating that it is to be used only for treatments around the eyes, at wavelengths between about 1400 nm and about 1600 nm and at energies less than about 10 mJ. A controller reading this information can send control signals to one or more optical energy sources to produce wavelengths in the range of 1400-1600 nm and with energies no greater than 10 mJ. A treatment provider can be notified via an interface unit, such as a monitor, that the handpiece is primarily for use around eyes, but the user can be offered the option to manually change treatment parameters such as the wavelength and/or energy, among others.

Co-pending U.S. application Ser. Nos. 11/223,787 and 60/800,075, each assigned to Reliant Technologies, Inc., and entitled "Interchangeable Tips for Medical Laser Treatments and Methods for Using Same", filed on Sep. 8, 2005 and Jul. 13, 2006 respectively, describe tips with a security chip and/or a memory which can be interchangeably attached to a handpiece, both of which are incorporated by reference in their entireties.

In one embodiment of the present invention, the optical energy delivery system component of the handpiece is configured to deliver the beam of optical energy in a fractional manner to a portion of tissue. Fractional treatment methods involve the generation of a large number of treatment zones within a portion of tissue. In fractional optical energy based treatments, the optical energy impacts directly on only a number of relatively small zones, instead of impacting directly on a larger portion of tissue undergoing treatment, as it does in conventional bulk treatments. Thus, a portion of skin treated using optical energy delivered in a fractional manner is composed of a plurality of zones where the tissue has been coagulated and/or necrosed by the optical energy, where the plurality of zones are contained within a larger volume of tissue that has not been coagulated and/or necrosed by the optical energy. Fractional treatment methods make it possible to leave substantial volumes of tissue uncoagulated and/or viable within a portion of tissue undergoing treatment. Co-pending U.S. application Ser. No. 10/367,582, entitled "Method And Apparatus For Treating Skin Using Patterns Of Optical Energy", filed on Feb. 14, 2003, and co-pending U.S. application Ser. No. 10/888,356, entitled "Method And Apparatus For Fractional Photo Therapy Of Skin", filed on Jul. 9, 2004, each assigned to Reliant Technologies, Inc., describe the use of fractional laser therapy and the value of discrete microscopic treatment zones with untreated tissue left between such zones, both of which applications are incorporated herein by reference in their entireties.

In optical energy treatments which produce microscopic lesions or treatment zones (i.e. less than about 500 microns in diameter, or between about 50 and about 200 microns, typically measured at the largest necrotic zone lesion dimension perpendicular to the optical axis of the treatment beam), various parameters are important to producing the desired and effective treatment results. For example, important parameters can include one or more of the following: the wavelength of the optical energy transmitted to the tissue; the size of the treatment spot at the tissue surface; the focal depth of the beam of optical energy, typically measured from the tissue surface or the surface of the contact surface of the handpiece and/or handpiece component; the amount of heating and/or cooling at the tissue surface; and the configuration of the exit window or aperture for the handpiece and/or handpiece component (e.g., tip, roller, contact or non-contact windows, window or aperture shape).

Optical energy devices that use optical energy beams with dimensions (e.g., beam width and/or beam diameter) of less than 500 μm typically use higher treatment fluences of optical energy than systems with larger beam sizes. The higher fluences can cause damage to the handpiece and/or tip window that can cause significant scattering, which is also more significant for microscopic spot sizes and can cause under-treatment or inconsistent treatment. Therefore, it can be useful to store handpiece and/or handpiece component usage data in the handpiece characteristic data storage system so that the device can verify that delivery systems and/or handpiece components are replaced after a defined amount of usage. The handpiece and/or handpiece component usage data can be stored securely on the handpiece in the memory using an encryption algorithm.

The optical energy delivery system can also be configured to allow for control of the microscopic treatment patterns and density of the treatment zones. A substantially uniform pre-selected pattern and density of the treatment zones across the entire treated portion of tissue can be achieved by controlling the optical energy delivery system.

As previously discussed, in addition to handpiece, the present invention is directed to devices which can be used to deliver optical energy. These devices comprise at least one optical energy source; at least one controller; and at least one handpiece, wherein each handpiece comprises at least one optical energy delivery system, and at least one handpiece characteristic data storage system which electronically stores characteristic data. In one example of the device, the at least one optical energy source and the at least one handpiece are configured to be repeatedly reconnected to each other; the at least one optical energy source and the at least one handpiece are configured such that, when operably coupled to each other, the at least one optical energy source produces a beam of optical energy that exits an emissive end of the at least one optical energy source, enters an ingressive end of at least one handpiece, passes through the optical energy delivery system, and passes out of an emissive end of the handpiece. In another example, the at least one controller of the device is configured to control the at least one optical energy source and the at least one handpiece; and the at least one controller is configured to adjust at least one parameter setting of the at least one optical energy source and/or the at least one handpiece based characteristic data in order to adjust the at least one optical energy source and the at least one handpiece so that they function together. The devices of the present invention can comprise optical energy based medical and/or cosmetic treatment devices. In one example, an optical energy based medical and/or cosmetic treatment device can comprise a device for dermatological treatment.

The devices of the present invention comprise at least one optical energy source. The at least one optical energy source can produce at least one of various forms of optical energy. The form of optical energy can be coherent in nature, such as laser radiation, or non-coherent in nature, such as flash lamp radiation. Coherent optical energy can be produced by lasers, including gas lasers, dye lasers, metal-vapor lasers, fiber lasers, diode lasers, and/or solid-state lasers. If a laser is used for the source of optical energy, the type of laser used with this invention can be selected from the group consisting of an argon ion gas laser, a carbon dioxide (CO2) gas laser, an excimer chemical laser, a dye laser, a neodymium yttrium aluminum garnet (Nd:YAG) laser, an erbium yttrium aluminum garnet (Er:YAG) laser, a holmium yttrium aluminum garnet (Ho:YAG) laser, an alexandrite laser, an erbium doped glass laser, a neodymium doped glass laser, a thulium doped glass laser, an erbium-ytterbium co-doped glass laser, an erbium doped fiber laser, a neodymium doped fiber laser, a thulium doped fiber laser, an erbium-ytterbium co-doped fiber laser, and combinations thereof. As previously discussed, the optical energy can be applied in a fractional manner to produce fractional treatment. For example, the FRAXEL RE:STORE™ laser (Reliant Technologies, Inc. Mountain View, Calif.) produces fractional treatments using an erbium-doped fiber laser operating at a wavelength that is primarily absorbed by water in tissue, at about 1550 nm.

In another embodiment, the optical energy source of the device can comprise an array of optical energy sources and/or a set of interchangeable optical energy sources. The array and/or set of optical energy sources can be housed in the same housing, or can be housed separate from each other. Each optical energy source in a set can be individually characterized to determine its optical energy source characteristic data, or each optical energy source in a set can be individually characterized in conjunction with a handpiece to determine combined optical energy source/handpiece characteristic data. Each of the optical energy sources in a set can be configured to deliver optical energy at a specific wavelength or wavelengths, to deliver optical energy of a wavelength or wavelengths appropriate for treating a specific disease or condition in tissue, or to deliver optical energy of a wavelength or wavelengths appropriate for treating a specific target in tissue.

The wavelength of the optical energy produced by the source can be between about 200 nm and about 20,000 nm. The wavelength of the optical energy can be selected based on the absorption strength of various components within the tissue and the scattering strength of the tissue. The wavelength of the optical energy can be chosen to target a particular absorbing species, such as, for example, water, elastin, collagen, sebum, hemoglobin, myoglobin, melanin, keratin, or other endogenous or exogenous molecules present in the tissue. Wavelengths that are primarily absorbed by water present in the tissue, such as, for example, 1550 nm, can be used. The wavelength of the optical energy treatment can be within the near infrared spectrum, such as, for example, between about 700 nm and about 1400 nm. Wavelengths in the visible spectrum, such as, for example, between about 400 nm and about 700 nm are also useful. Ultraviolet optical energy within the range of between about 200 nm to about 400 nm can be used. These wavelengths can be particularly effective for allowing lower levels of radiation to be used to activate photodynamic therapeutic agents for treatment of conditions in the papillary and reticular dermis.

Depending on the desired size and depth of the treatment zones, the wavelength of the optical energy used can be selected from the group consisting of between about 1100 nm and about 2500 nm, between about 1280 nm and about 1350 nm, between about 1400 nm and about 1500 nm, between about 1500 nm and about 1620 nm, between about 1780 nm and 2000 nm, and combinations thereof. Wavelengths longer than 1500 nm and wavelengths with absorption coefficients in water of between about $1\ cm^{-1}$ and about $30\ cm^{-1}$ can be used if the goal is to get deep penetration with small treatment zones. The shorter wavelengths generally have higher scattering coefficients than the longer wavelengths.

In some examples, the optical energy source is capable of generating optical energy at wavelengths with high absorption in water. Cellular water absorbs optical energy and transforms the optical energy into heat. Wavelengths larger than 190 nm, such as wavelengths in the range from 190 nm to 10600 nm, from 700 nm to 1600 nm, and about 1550 nm can used. One example of an optical energy source is an erbium-based fiber laser designed for about 1550 nm range operation. The source of optical energy can be capable of providing one wavelength or a range of wavelengths or can be tunable across a range of wavelengths. One or more sources of optical energy can be powered by a power source to produce a variety of different wavelengths or wavelength ranges used in a dermatological treatment. The optical energy source can be adapted to selectively produce pulses of laser light at a frequency of between about 0 and about 50,000 pulses per second, or between about 0 and about 1,000 pulses per second. In one example, an optical energy source can emit a beam having pulse energy per treatment spot of between about 1 mJ and about 1000 mJ, or between about 10 mJ and about 30 mJ, with each pulse having a pulse duration per treatment spot between about 0.1 ms and about 30 ms, or about 1 ms.

In some embodiments of the present invention, the device can comprise an optical energy based medical and/or cosmetic treatment device. The medical and/or cosmetic treatment device can be used, for example, for non-ablative coagulation of an epidermal and/or a dermal layer of a target portion of tissue. Typically, for this purpose, a local optical fluence greater than about 5 $J/cm^2$, or an optical fluence in the range from about 10 $J/cm^2$ to about 1000 $J/cm^2$, is adequate for coagulating tissue. Generally, the local optical fluence is adapted to the wavelength and the tissue to be treated. If various dermatological effects are desired, an optical energy device can be used which has the capacity to produce effects suitable for other types of tissue treatment. For example, if ablation of an epidermal layer of the target portion of tissue is desired, a device can be used with the capability to emit a beam of optical energy with a wavelength of about 2940 nm and local optical fluence higher than about 10 $J/cm^2$.

Examples of improved laser treatment devices and methods employing robotics and motion control feedback are found in U.S. Pat. No. 7,282,060 assigned to Reliant Technologies, Inc., and entitled "Method And Apparatus For Monitoring And Controlling Laser-Induced Tissue Treatment", which is incorporated herewith by reference in its entirety. These embodiments typically use a light-emitting diode (LED) or some other illumination source to illuminate the tissue so that it can be more easily detected.

In one embodiment, the device can comprise at least one optical energy source characteristic compensation system configured to be controlled by the controller. The source characteristic compensation system is a system that can be adjusted by the controller as needed to alter the beam path or to direct, focus or collimate the beam of optical energy in order to align a handpiece with an optical energy source. The source characteristic compensation system can be implemented using one or more optical elements, such as, for example, a mirror, a lens, a prism, a reflector mechanism, a scanner mechanism, an optical window, a rotating optical element, a counter-rotating wheel element, an electro-optic element, an acousto-optic element, and combinations thereof.

In another embodiment, the device can further comprise one or more transmission systems for delivering a beam of optical energy from the emissive end of an optical energy system and/or source to the ingressive end of a handpiece. The transmission system can be configured to be connected, disconnected and/or reconnected to the emissive end of an optical energy system and/or source, and/or to the ingressive end of a handpiece. The transmission system can be configured to be used interchangeably with other devices for delivering a beam of optical energy. The transmission system can comprise a waveguide, an optical fiber, an articulated arm, and combinations thereof. The transmission system can further comprise a protective housing. The transmission system can further comprise one or more electronic connections in order to electronically couple a handpiece with a controller. The electronic connections can comprise electrical wires, contacts and/or cables.

In another embodiment, the device can further comprise one or more power sources. The power source can be located in the same housing, or in a separate housing, as the optical energy system and/or source. The device can further comprise a cooling unit or a chiller, which is used to reduce the surface temperature of a tissue before, during or immediately following a treatment. The cooling unit or chiller can be located in the same housing, or in a separate housing, as the optical energy source.

In another embodiment, the device can further comprise a user input/output (I/O) interface. The input/output interface can be included in or attached to the optical energy system and/or source so that a user can interact with, control and receive information from the optical energy system. In yet another embodiment, the device can further comprise a calibration port. The calibration port can be configured to operate in conjunction with more than one handpiece and/or optical energy system and/or source, or can be configured to operate with only one optical energy system and/or source and handpiece.

The device of the present invention can be configured to deliver a treatment while the handpiece is substantially stable, or while the handpiece is in motion. The device can be configured to deliver a treatment while the optical energy source is operated in a continuous mode, or in a pulsed mode. The device can be configured to electronically collect characteristic data while the optical energy source is operated in a continuous mode or in a pulsed mode.

In addition to handpieces and devices, the present invention is directed to methods of using the handpieces and/or devices, including methods of characterizing an optical energy system and/or source, methods of characterizing a handpiece, methods of characterizing a handpiece in combination with an optical energy system and/or source, and methods of adjusting a handpiece and an optical energy system and/or source.

In one example, the present invention is directed to a method of characterizing a component for use in an optical energy treatment device, comprising determining characteristic data of a beam and/or beam path as the beam of optical energy enters, passes through and/or exits the component; and electronically storing the characteristic data in a characteristic data storage system. In one example, the component comprises an optical energy system and/or source, the characteristic data is determined as the beam and/or beam path exits the optical energy system and/or source, and the characteristic data storage system comprises an optical energy system and/or source characteristic data storage system. In one example, the component comprises a handpiece; the characteristic data is determined as the beam enters the ingressive end of the handpiece, enters a component of the handpiece, exits the component of the handpiece, and/or exits the emissive end of the handpiece; and the characteristic data storage system comprises a handpiece characteristic data storage system. In another example, the component comprises an optical energy transmission system, the characteristic data is determined as the beam and/or beam path enters the ingressive end of the transmission system and/or exits the emissive end of the transmission system, and the characteristic data storage system comprises a transmission system characteristic data storage system.

In one example, the stored characteristic data further comprises information about the component that is not determined during the determining step. In another example, the step of determining characteristic data of a beam and/or beam path comprises characterizing a deviation of a beam and/or beam path from an optimal beam and/or beam path. In another example, the step of determining characteristic data comprises characterizing a pointing error, an eccentricity, a beam diameter, and/or a wavefront curvature.

In one example, the method further comprises the step of converting at least one piece of the characteristic data from a distance-based value to a time-based value, or from a time-based value to a distance-based value. In another example, the step of determining characteristic data comprises the step of converting a deviation from a distance-based value to a time-based value comprises calculating a beam pulse delay, a beam pulse duration, and/or a beam pulse pattern repetition rate that would compensate for the deviation of the beam and/or beam path and allow the beam and/or beam pulse to be aligned at least partially with a optimal beam path and/or position within a pre-determined tolerance.

In another example, the step of determining characteristic data comprises the step of determining a deviation of a beam of optical energy from an optimal beam in frequency, duration and or/delay as the beam exits the optical energy source and/or system. In another example, the step of determining characteristic data of a handpiece comprises characterizing a deviation of a beam parameter from an optimal beam parameter as a beam of optical energy enters the ingressive end of a handpiece, passes through the handpiece and an optical energy delivery system, and exits the emissive end of the handpiece; and electronically collecting the handpiece characteristic data. In yet another example, the step of determining characteristic data comprises determining characteristic data of a handpiece in combination with an optical energy source and/or system by attaching a handpiece to an optical energy source and/or system; passing a beam of optical energy emanating from an emissive end of the optical energy source and/or system into the ingressive end of the handpiece, through the handpiece and an optical energy delivery system, and out the emissive end of the handpiece; determining the characteristics of the handpiece, thereby producing handpiece characteristic data; and electronically collecting the handpiece characteristic data; wherein the characterizing comprises characterizing a deviation of a beam path from an optimal position in both a direction and a magnitude, and characterizing a deviation of a beam timing from an optimal beam frequency, duration and or/delay. The method can further comprise the step of electronically recording the deviation in the beam path and/or the beam timing as a value based on a distance measurement and/or a time measurement in a data storage system. The method can further comprise the step of electronically converting the deviation in the beam path and/or the beam timing from a distance to a time and/or from a time to a distance. The method can further comprise the step of electronically manipulating the characteristic data so as to remove or separate data such as, for example, optical source characteristic data from handpiece characteristic data. The characteristic can be characterized during or following the manufacture of the component and/or the optical energy based treatment device as a whole.

In yet a further embodiment, the method of the present invention is directed to a method of adjusting a handpiece and an optical energy system and/or source for use in an optical energy treatment device, comprising: attaching a handpiece to an optical energy system and/or source, accessing characteristic data stored in a handpiece characteristic data storage system, determining at least one parameter setting based on the characteristic data stored in the handpiece characteristic data storage system, and adjusting at least one operational parameter of the handpiece and/or of the optical energy system and/or source based on at least one determined parameter setting. In one example, the method can further comprise the step of accessing characteristic data stored in an optical energy system and/or source characteristic data storage system, and determining at least one parameter setting based on the characteristic data stored in the optical energy system and/or source characteristic data storage system. In another example, the method wherein the step of determining comprises converting the characteristic data from a distance-based value to a time-based value, or from a distance-based value to a time-based value.

In another example, the method is a method of adjusting an optical energy source and/or system and handpiece for use in a device, comprising: determining the characteristic data of a handpiece; electronically storing the handpiece characteristic data in a handpiece characteristic data storage system; operably connecting an optical energy source and/or system to the handpiece; electronically accessing the handpiece characteristic data stored in the handpiece characteristic data storage system; determining an adjustment to at least one parameter setting based on the stored handpiece characteristic data; and adjusting the at least one functional parameter based on the determined parameter setting in order to adjust the optical energy source and/or the handpiece so they function together within a pre-determined tolerance.

The method can further comprise the step of determining characteristic data of the handpiece in combination with the optical energy system and/or source, thereby generating combined optical energy source/handpiece characteristic data. The method can further comprise the step of electronically manipulating the combined optical energy source/handpiece characteristic data, producing optical source characteristic data and/or handpiece characteristic data. The method can further comprise the step of determining characteristic data of the optical energy system and/or source, thereby generating optical energy source characteristic data.

In one example, the step of determining the adjustment further comprises using combined optical energy source/handpiece characteristic data and/or optical energy source characteristic data. In another example, the step of adjusting comprises adjusting at least one of a functional parameter so that a deviation of a beam path of a beam of optical energy in both direction and distance is oriented along a line of motion of a scanner and in a positive direction of motion of the scanner. In another example, the step of adjusting comprises adjusting a functional parameter of the optical energy system and/or source selected from the group consisting of a pulse duration, a pulse timing, a mirror position, a lens position, and combinations thereof. In another example, the step of adjusting comprises adjusting a functional parameter of a handpiece selected from the group consisting of a scanner speed, a scanner facet time, a delay time, a mirror position, a lens position, and combinations thereof.

In one example, the step of determining characteristic data of the optical energy source and/or system comprises generating optical energy source characteristic data describing a characteristic profile of the optical energy source and/or system. In another example, the step of determining characteristic data of the optical energy source and/or system comprises characterizing a deviation of beam and/or a beam path from an optimal position in both direction and distance as the beam and/or beam path exits the optical energy source and/or system.

In one example, the step of determining characteristic data of the handpiece comprises generating characteristic data describing a characteristic profile of the handpiece and/or the optical delivery system and/or source. In another example, the step of determining characteristic data of the handpiece comprises characterizing a deviation of a beam and/or beam path from an optimal position in both direction and distance when the beam is passed through the handpiece, including the optical delivery system. In another example, the handpiece characteristic data is removed from the combined optical energy source/handpiece characteristic data in order to generate the optical energy source characteristic data.

In one example, the step of electronically storing the characteristic data in a characteristic data storage system comprises storing the characteristic data as a distance-based value. In another example, the step of electronically storing the characteristic data in a characteristic data storage system comprises storing the characteristic data as a time-based value. In yet another example, the step of electronically storing the characteristic data in a characteristic data storage system comprises storing the characteristic data as an angle.

In one example, the step of determining an adjustment comprises using a controller to electronically access stored characteristic data and using an algorithm and/or a lookup table to determine a parameter setting. In another example, the step of determining an adjustment comprises electronically converting the characteristic data from a time-based value to a distance-based value, and/or from a distance-based value to a time-based value, and using the converted characteristic data to determine a parameter setting. In another example, the step of determining an adjustment comprises electronically manipulating characteristic data to determine a parameter setting. In yet another example, the step of determining an adjustment comprises electronically generating at least one parameter setting for at least one functional parameter.

In one example, the method further comprises the step of electronically storing optical energy source characteristic data in an optical energy source characteristic data storage system. In another example, the method further comprises the step of adjusting at least one optical energy source characteristic compensation system. In another example, the method further comprises the step of adjusting at least one characteristic compensation system.

Embodiments of the present invention include handpieces, devices, and methods of characterizing, adjusting and using delivery systems and devices which comprise handpiece characteristic data storage systems storing characteristic data, wherein the handpieces, devices and methods described herein can be used in conjunction with the inventions and embodiments described in the above-referenced co-pending patent applications. However, handpiece embodiments described herein are not limited solely to use in conjunction with the aforementioned patent applications or the inventions described therein.

Although the detailed description contains many specifics, these should not be construed as limiting the scope of the invention but merely as illustrating different examples and aspects of the invention. It should be appreciated that the scope of the invention includes other embodiments not discussed in detail above. Various modifications, changes and variations which will be apparent to those skilled in the art may be made in the arrangement, operation and details of the methods and devices of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

All publications, patents and patent applications cited herein, whether supra or infra, are hereby incorporated by reference in their entirety.

In the specification and in the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

The invention claimed is:

1. A treatment device comprising:
   at least one optical energy source;
   at least one controller; and
   at least one handpiece, each handpiece comprising at least one optical energy delivery system configured to direct optical energy at a portion of tissue to be treated, and a first data storage system which electronically stores characteristic data relating to the handpiece;

at least one tip, each tip configured to be removably coupled with the at least one handpiece, and each tip including a pathway configured to transfer the beam from the handpiece to the portion of tissue when the tip is coupled with the handpiece;

wherein the at least one handpiece is configured to be repeatedly reconnected to the device;

the at least one optical energy source and the at least one handpiece are configured such that, when one handpiece of the at least one handpiece and the at least one energy source are operably coupled, the at least one optical energy source produces a beam of optical energy that exits an emissive end of the at least one optical energy source, enters an ingressive end of the one handpiece, passes through the at least one optical energy delivery system of the one handpiece, and exits an emissive end of the one handpiece in order to treat a portion of tissue;

the at least one controller is configured to control the at least one optical energy source and the at least one handpiece, to access the characteristic data stored in the first data storage system, and to adjust one or more functional parameters of the at least one optical energy source or one or more functional parameters of the at least one handpiece based on the characteristic data in order for the at least one handpiece to operate with the at least one optical energy source within a pre-determined tolerance; and the at least one optical energy delivery system comprises a starburst scanner, and the controller is configured to adjust the at least one optical energy source so that a deviation of a beam path of a beam of optical energy produced by the at least one optical energy source is oriented along a line of motion of the starburst scanner and in a positive direction of motion of the starburst scanner, in order for an adjustment of a pulse delay time to compensate for the deviation of the beam path and for the at least one handpiece and the at least one optical energy source to function together within a pre-determined tolerance.

2. The device of claim 1, wherein the at least one optical energy source comprises a laser.

3. The device of claim 1, wherein the at least one optical energy source comprises an array of optical energy sources.

4. The device of claim 1, wherein the at least one optical energy source comprises a set of interchangeable optical energy sources.

5. The device of claim 4, wherein each of the optical energy sources in the set is individually characterized to determine the characteristic data.

6. The device of claim 4, wherein each of the optical energy sources in the set is configured to deliver optical energy at a different wavelength.

7. The device of claim 4, wherein each of the optical energy sources in the set is configured to deliver optical energy of a wavelength appropriate for treating a specific disease or condition in tissue.

8. The device of claim 4, wherein each of the optical energy sources in the set is configured to deliver optical energy of a wavelength appropriate for treating a specific target in tissue.

9. The device of claim 1, wherein the at least one optical energy source further comprises at least one source characteristic compensation system configured to be controlled by the at least one controller.

10. The device of claim 1, wherein the at least one controller is configured to use characteristic data to determine at least one parameter setting that allows the at least one optical energy source and one handpiece of the at least one handpiece to function together within a pre-determined tolerance.

11. The device of claim 10, wherein the at least one controller is configured to adjust the one or more functional parameters of the at least one optical energy source or the one or more functional parameters of the at least one handpiece to match the determined at least one parameter setting within a pre-determined tolerance.

12. The device of claim 1, wherein the at least one controller is configured to electronically convert the characteristic data from a time-based value to a distance-based value, or the characteristic data from a distance-based value to a time-based value.

13. The device of claim 1, wherein the at least one controller is configured to electronically collect the characteristic data.

14. The device of claim 1, wherein the at least one controller is configured to electronically record characteristic data in the first data storage system.

15. The device of claim 1, wherein the at least one controller is configured to electronically remove optical energy source characteristic data from combined optical energy source/handpiece characteristic data so as to convert the combined optical energy source/handpiece characteristic data to handpiece characteristic data.

16. The device of claim 1, wherein the at least one controller is configured to electronically access the characteristic data stored in the first data storage system of the at least one handpiece, and use the characteristic data to determine at least one parameter setting that allows the at least one optical energy source and the at least one handpiece to function together within a pre-determined tolerance.

17. The device of claim 1, wherein the at least one controller is configured to electronically collect characteristic data for the at least one optical energy source, access the characteristic data stored in the first data storage system of the at least one handpiece, and use the characteristic data collected from the at least one optical energy source and the characteristic data stored in the first data storage system to determine at least one parameter setting that allows the at least one optical energy source and the at least one handpiece to function together within a pre-determined tolerance.

18. The device of claim 1, further comprising:
a second data storage system which stores characteristic data relating to the at least one optical energy source and which is configured to be controlled by the at least one controller.

19. The device of claim 18, wherein the at least one controller is configured to electronically access the characteristic data stored in the second data storage system, access the handpiece characteristic data stored in the first data storage system of the at least one handpiece, and use the characteristic data relating to the at least one optical energy source or the characteristic data relating to the at least one handpiece to calculate at least one parameter setting that allows the at least one optical energy source and the at least one handpiece to function together within a predetermined tolerance.

20. The device of claim 1, wherein the at least one optical energy source or the at least one controller are configured to be repeatedly reconnectable to the device and to be interchangeable.

21. The device of 1, wherein the device is configured to treat the portion of tissue in a fractional manner.

22. The device of claim 1, further comprising: at least one reconnectable transmission system for delivering the beam of optical energy from the emissive end of the optical energy source to the ingressive end of the handpiece.

23. The device of claim 22, wherein the transmission system comprises a an optical fiber.

24. The device of claim 1, wherein the device is configured to deliver a treatment when the at least one handpiece is in motion.

25. The device of claim 1, wherein the device is configured to deliver a treatment when the at least one handpiece is not in motion.

* * * * *

UNITED STATES PATENT AND TRADEMARK OFFICE
CERTIFICATE OF CORRECTION

PATENT NO.         : 8,523,847 B2                                              Page 1 of 1
APPLICATION NO.    : 12/264793
DATED              : September 3, 2013
INVENTOR(S)        : David Dewey et al.

It is certified that error appears in the above-identified patent and that said Letters Patent is hereby corrected as shown below:

In the Specification:

Column 3, line number 33, after "using" delete "a".

Column 9, line number 47, after "to" delete "can".

Column 13, line number 65, after "order" insert --for--.

Column 15, line number 45, after "characteristic" insert --data--.

Column 18, line number 52, after "optical connections," delete "optical connections," and at line number 59 change "an" to --a--.

Column 19, line number 7, change the second occurrence of "a" to --the actual beam and/or beam path--.

Column 21, line number 52, change "etc," to --etc.,--.

Column 22, line number 44, after "used" delete "with".

Signed and Sealed this
Twenty-eighth Day of January, 2014

Michelle K. Lee
*Deputy Director of the United States Patent and Trademark Office*